(12) United States Patent
Zong

(10) Patent No.: US 11,739,118 B2
(45) Date of Patent: Aug. 29, 2023

(54) AFFINITY CHROMATOGRAPHY LIGANDS WITH MILD ELUTION PH

(71) Applicant: Bioprocessia Technologies LLC, San Diego, CA (US)

(72) Inventor: Yinong Zong, San Diego, CA (US)

(73) Assignee: Bioprocessia Technologies LLC, San Diego, CA (US)

( * ) Notice: Subject to any disclaimer, the term of this patent is extended or adjusted under 35 U.S.C. 154(b) by 800 days.

(21) Appl. No.: 16/485,854

(22) PCT Filed: Mar. 31, 2017

(86) PCT No.: PCT/US2017/025335
§ 371 (c)(1),
(2) Date: Aug. 14, 2019

(87) PCT Pub. No.: WO2018/151743
PCT Pub. Date: Aug. 23, 2018

(65) Prior Publication Data
US 2019/0375785 A1 Dec. 12, 2019

Related U.S. Application Data

(60) Provisional application No. 62/459,394, filed on Feb. 15, 2017.

(51) Int. Cl.
| | | |
|---|---|---|
| *C07K 1/22* | (2006.01) | |
| *B01D 15/38* | (2006.01) | |
| *B01J 20/289* | (2006.01) | |
| *B01J 20/32* | (2006.01) | |
| *C07K 14/31* | (2006.01) | |
| *C07K 14/315* | (2006.01) | |
| *C07K 16/06* | (2006.01) | |

(52) U.S. Cl.
CPC ............ *C07K 1/22* (2013.01); *B01D 15/3804* (2013.01); *B01J 20/289* (2013.01); *B01J 20/3219* (2013.01); *B01J 20/3274* (2013.01); *C07K 14/31* (2013.01); *C07K 14/315* (2013.01); *C07K 16/065* (2013.01); *B01J 2220/52* (2013.01); *C07K 2319/21* (2013.01); *C07K 2319/30* (2013.01)

(58) Field of Classification Search
CPC ........ C07K 1/22; C07K 14/31; C07K 14/315; C07K 16/065; B01D 15/3804; B01J 20/289; B01J 20/3219
See application file for complete search history.

(56) References Cited

U.S. PATENT DOCUMENTS

| | | | |
|---|---|---|---|
| 8,329,860 B2 | 12/2012 | Hall et al. | |
| 9,382,297 B2 | 7/2016 | Honda et al. | |
| 2010/0322929 A1 | 12/2010 | Zurawski | |
| 2011/0098217 A1 | 4/2011 | DiMarchi et al. | |
| 2011/0104163 A1* | 5/2011 | Dimitrov | A61K 38/1774 |
| | | | 424/134.1 |
| 2011/0266225 A1 | 11/2011 | Johansson et al. | |
| 2012/0059145 A1 | 3/2012 | Altman | |
| 2013/0177568 A1 | 7/2013 | Bhatt et al. | |
| 2013/0274451 A1 | 10/2013 | Bjorkman et al. | |
| 2016/0185826 A1* | 6/2016 | Lin | C12N 7/00 |
| | | | 435/235.1 |
| 2016/0207966 A1 | 7/2016 | Ander et al. | |
| 2016/0237124 A1* | 8/2016 | Qian | C07K 16/00 |
| 2016/0280744 A1 | 9/2016 | Honda et al. | |
| 2019/0375785 A1 | 12/2019 | Zong | |

FOREIGN PATENT DOCUMENTS

| | | | | |
|---|---|---|---|---|
| CN | 105377880 A | | 3/2016 | |
| WO | WO-2008039141 A1 * | | 4/2008 | ......... B01D 15/3809 |
| WO | WO-2017194596 A1 * | | 11/2017 | ......... B01D 15/3809 |

OTHER PUBLICATIONS

Chen et al. "Fusion protein linkers: property, design and functionality" Adv Drug Deliv Rev. Oct. 15, 2013; 65(10: 1357-1369 (Year: 2013).*
Klein et al. "Design and characterization of structured protein linkers with differing flexibilities" Protein engineering design & selection, 27(10, pp. 325-330, 2014. (Year: 2014).*
Tsukamoto et al. "Engineered protein A ligands, derived form histidine-scanning library, facilitate the affinity purification of IgG under mild acidic conditions" J. Biological Engineering, 2014, 8:15 (Year: 2014).*
Gagnon et al., "Conformational plasticity of IgG during protein A affinity chromatography," Journal of Chromatography A, Feb. 12, 2016, 1433:98-105.
Gülich et al., "Protein engineering of an IgG-binding domain allows milder elution conditions during affinity chromatography," Journal of Biotechnology, Jan. 21, 2000, 76(2-3):233-43.
Hoffman et al., "Crystal structure of prokaryotic ribosomal protein L9: a bi-lobed RNA-binding protein," The EMBO Journal, Jan. 1994, 13(1):205-12.
Kimple et al., "Overview of affinity tags for protein purification," Current Protocols in Protein Science, Aug. 2013, 73:9.9.1-9.9.23.
Latypov et al., "Elucidation of acid-induced unfolding and aggregation of human immunoglobulin IgG1 and IgG2 Fc," Journal of Biological Chemistry, Jan. 6, 2012, 287(2):1381-96.
Magdeldin et al., "Affinity chromatography: Principles and applications," Affinity Chromatography, Mar. 21, 2012, 1-28.
Nilsson et al., "A synthetic IgG-binding domain based on staphylococcal protein A. Protein Engineering, Design and Selection," Feb. 1, 1987, 1(2):107-13.
Pabst et al., "Engineering of novel Staphylococcal protein A ligands to enable milder elution pH and high dynamic binding capacity," Journal of Chromatography A, Oct. 3, 2014, 1362:180-5.

(Continued)

*Primary Examiner* — Daniel E Kolker
*Assistant Examiner* — James L Rogers
(74) *Attorney, Agent, or Firm* — Fish & Richardson P.C.

(57) ABSTRACT

The disclosure relates to chromatography ligands, e.g., chromatography ligands comprising at least two binding units and at least one spacer domain, wherein each binding unit comprises one or two immunoglobulin binding domains.

19 Claims, 17 Drawing Sheets

Specification includes a Sequence Listing.

(56) References Cited

OTHER PUBLICATIONS

PCT International Preliminary Report on Patentability in International Appln. No. PCT/US2017/25335, dated Aug. 20, 2019, 11 pages.
PCT International Search Report and Written Opinion in International Appln. No. PCT/US2017/25335, dated Oct. 4, 2017, 20 pages.
Weidner et al., "Expression of recombinant proteins in the methylotrophic yeast *Pichia pastoris*," JoVE (Journal of Visualized Experiments), Feb. 25, 2010, (36):e1862, 5 pages.
Xia et al., "Molecular modification of protein A to improve the elution pH and alkali resistance in affinity chromatography," Applied Biochemistry and Biotechnology, Apr. 2014, 172(8):4002-12.
Chen et al., "Fusion protein linkers: property, design and functionality," Advanced Drug Delivery Reviews, Oct. 15, 2013, 65(10):1357-69.
CN Office Action in Chinese Appln. No. 201780088486.0, dated Aug. 25, 2022, 21 pages (with English translation).
Swanson et al., "Harnessing the unique structural properties of isolated α-helices," Journal of Biological Chemistry, Sep. 12, 2014, 289(37):25460-7.

* cited by examiner

```
B       -AD----NKFNKEQQNAFYEILHLPNLNEEQRNGFIQSLKDDPSQSANLLAEAKKLNDAQAPK  58
C       -AD----NKFNKEQQNAFYEILHLPNLNEEQRNGFIQSLKDDPSVSKEILAEAKKLNDAQAPK  58
A       -AD----NNFNKEQQNAFYEILNMPNLNEEQRNGFIQSLKDDPSQSANLLSEAKKLNESQAPK  58
E       -ADAQNNFNKDQQSAFYEILNMPNLNEEQRNGFIQSLKDDPSQSTNVLGEAKKLNESQAPK  61
D       AAN---AAQHDEAQQNAFYQVLNMPNLNADQRNGFIQSLKDDPSQSANVLGEAQKLNDSQAPK  60
Z       -VD----NKFNKEQQNAFYEILHLPNLNEEQRNAFIQSLKDDPSQSANLLAEAKKLNDAQAPK  58
Z_D36H  -VD----NKFNKEQQNAFYEILHLPNLNEEQRNAFIQSLKHDPSQSANLLAEAKKLNDAQAPK  58
```

FIG. 1

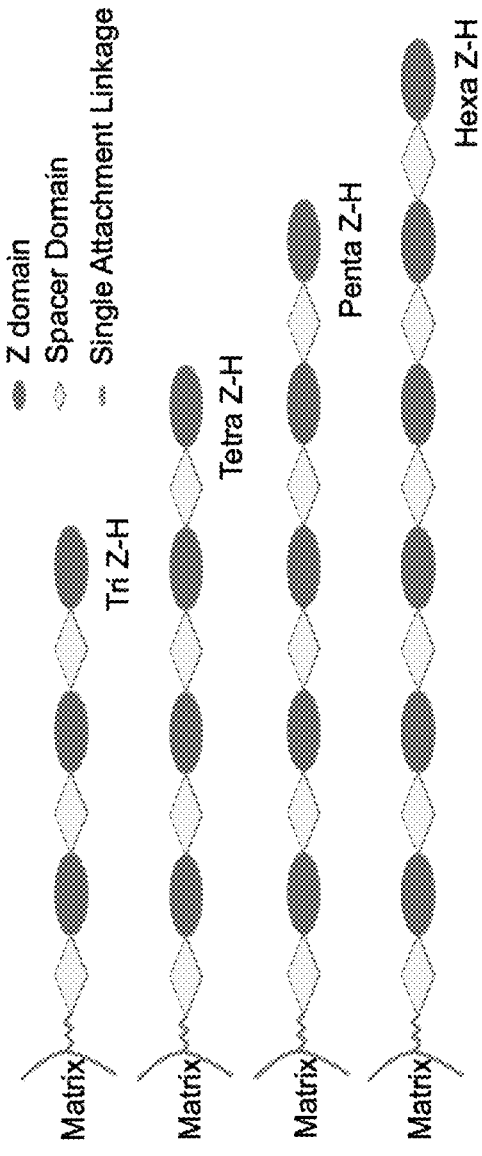

FIG. 2

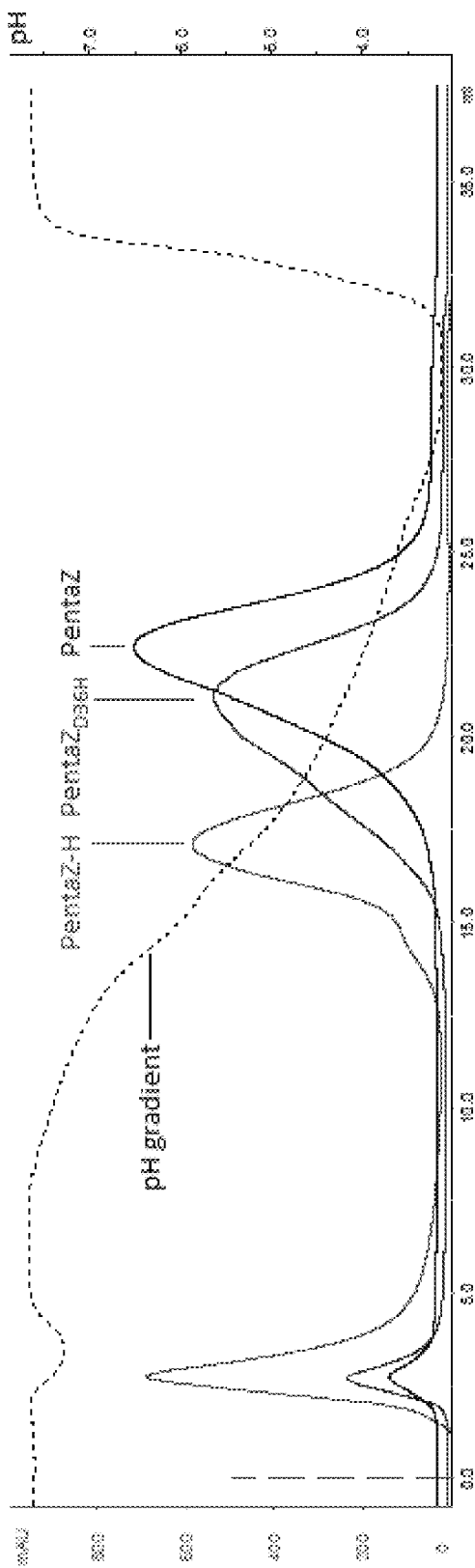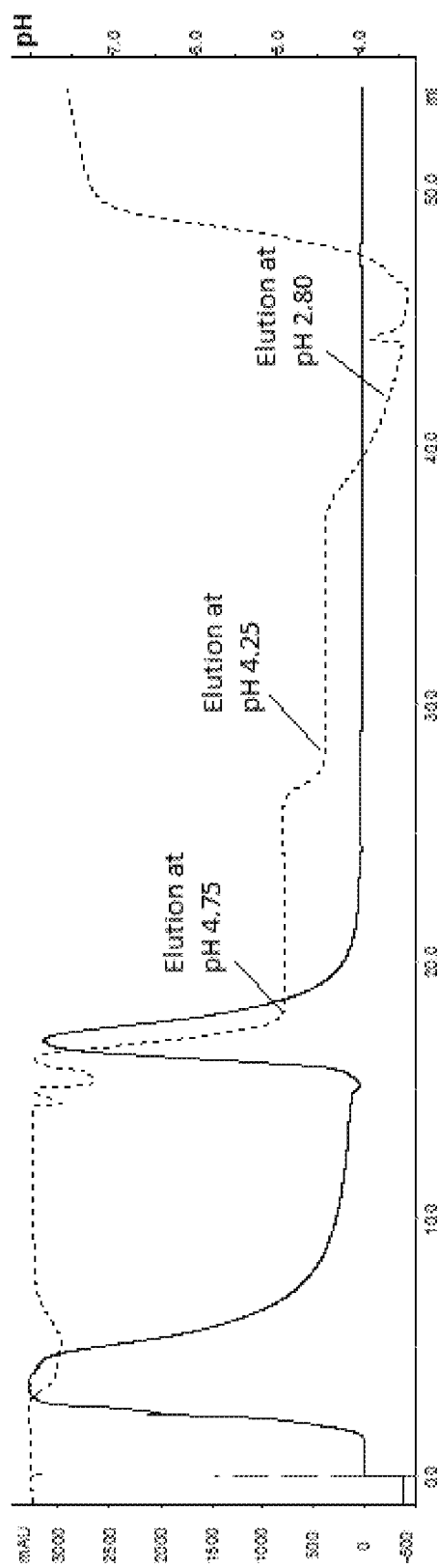
FIG. 6
FIG. 7

FIG. 9

```
SEQ ID NO:1
LIENGTH: 58
TYPE: PRT
ORGANISM: STAPHYLOCOCCUS AUREUS
OTHER INFORMATION: B DOMAIN WILD TYPE

Ala Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Gly Phe
                20                  25                  30

Ile Gln Ser Leu Lys Asp Asp Pro Ser Gln Ser Ala Asn Leu Leu
                35                  40                  45

Ala Glu Ala Lys Lys Leu Asn Asp Ala Gln Ala Pro Lys
                50                  55

SEQ ID NO:2
LIENGTH: 58
TYPE: PRT
ORGANISM: STAPHYLOCOCCUS AUREUS
OTHER INFORMATION: C DOMAIN WILD TYPE

Ala Asp Asn Lys Phe Asn Lys Glu Gln Gln Asn Ala Phe Tyr Glu
1               5                   10                  15

Ile Leu His Leu Pro Asn Leu Thr Glu Glu Gln Arg Asn Gly Phe
                20                  25                  30

Ile Gln Ser Leu Lys Asp Asp Pro Ser Val Ser Lys Glu Ile Leu
                35                  40                  45

Ala Glu Ala Lys Lys Leu Asn Asp Ala Gln Ala Pro Lys
                50                  55

SEQ ID NO:3
LIENGTH: 58
TYPE: PRT
ORGANISM: STAPHYLOCOCCUS AUREUS
OTHER INFORMATION: A DOMAIN WILD TYPE

Ala Asp Asn Asn Phe Asn Lys Glu Gln Gln Asn Ala Phe Tyr Glu
1               5                   10                  15

Ile Leu Asn Met Pro Asn Leu Asn Glu Glu Gln Arg Asn Gly Phe
                20                  25                  30
```

FIG. 9 (continued)

```
Ile Gln Ser Leu Lys Asp Asp Pro Ser Gln Ser Ala Asn Leu Leu
            35              40                      45

Ser Glu Ala Lys Lys Leu Asn Glu Ser Gln Ala Pro Lys
            50              55
```

SEQ ID NO: 4
LIENGTH: 60
TYPE: PRT
ORGANISM: Staphylococcus aureus
OTHER INFORMATION: D domain wild type

```
Ala Ala Asn Ala Ala Gln His Asp Glu Ala Gln Gln Asn Ala Phe
1               5               10                      15

Tyr Gln Val Leu Asn Met Pro Asn Leu Asn Ala Asp Gln Arg Asn
                20              25                      30

Gly Phe Ile Gln Ser Leu Lys Asp Asp Pro Ser Gln Ser Ala Asn
                35              40                      45

Val Leu Gly Glu Ala Gln Lys Leu Asn Asp Ser Gln Ala Pro Lys
                50              55                      60
```

SEQ ID NO: 5
LIENGTH: 61
TYPE: PRT
ORGANISM: Staphylococcus aureus
OTHER INFORMATION: E domain wild type

```
Ala Asp Ala Gln Gln Asn Asn Phe Asn Lys Asp Gln Gln Ser Ala
1               5               10                      15

Phe Tyr Glu Ile Leu Asn Met Pro Asn Leu Asn Glu Ala Gln Arg
                20              25                      30

Asn Gly Phe Ile Gln Ser Leu Lys Asp Asp Pro Ser Gln Ser Thr
                35              40                      45

Asn Val Leu Gly Glu Ala Lys Lys Leu Asn Glu Ser Gln Ala Pro
                50              55                      60

Lys
```

FIG. 9 (continued)

SEQ ID NO: 6
LIENGTH: 58
TYPE: PRT
ORGANISM: Artificial Sequence
OTHER INFORMATION: Z domain synthesized

```
Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys Asp Asp Pro Ser Gln Ser Ala Asn Leu Leu
                35                  40                  45

Ala Glu Ala Lys Lys Leu Asn Asp Ala Gln Ala Pro Lys
                50                  55
```

SEQ ID NO: 7
LIENGTH: 58
TYPE: PRT
ORGANISM: Artificial Sequence
OTHER INFORMATION: ZD36H domain synthesized

```
Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys His Asp Pro Ser Gln Ser Ala Asn Leu Leu
                35                  40                  45

Ala Glu Ala Lys Lys Leu Asn Asp Ala Gln Ala Pro Lys
                50                  55
```

SEQ ID NO: 8
LIENGTH: 18
TYPE: PRT
ORGANISM: Bacillus stearothermophilus
OTHER INFORMATION: Connecting Helix of ribosomal protein L9

```
Glu Ala Gln Lys Gln Lys Glu Gln Arg Gln Ala Ala Glu Glu Leu
1               5                   10                  15

Ala Asn Ala
```

FIG. 9 (continued)

```
SEQ ID NO: 9
LIENGTH: 301
TYPE: PRT
ORGANISM: Artificial Sequence
OTHER INFORMATION: PentaZ
```

| | | | | | | | | | | | | | | |
|---|---|---|---|---|---|---|---|---|---|---|---|---|---|---|
| Val | Asp | Asn | Lys | Phe | Asn | Lys | Glu | Gln | Gln | Asn | Ala | Phe | Tyr | Glu |
| 1 | | | | 5 | | | | | 10 | | | | | 15 |
| Ile | Leu | His | Leu | Pro | Asn | Leu | Asn | Glu | Glu | Gln | Arg | Asn | Ala | Phe |
| | | | | 20 | | | | | 25 | | | | | 30 |
| Ile | Gln | Ser | Leu | Lys | Asp | Asp | Pro | Ser | Gln | Ser | Ala | Asn | Leu | Leu |
| | | | | 35 | | | | | 40 | | | | | 45 |
| Ala | Glu | Ala | Lys | Lys | Leu | Asn | Asp | Ala | Gln | Ala | Pro | Lys | Val | Asp |
| | | | | 50 | | | | | 55 | | | | | 60 |
| Asn | Lys | Phe | Asn | Lys | Glu | Gln | Gln | Asn | Ala | Phe | Tyr | Glu | Ile | Leu |
| | | | | 65 | | | | | 70 | | | | | 75 |
| His | Leu | Pro | Asn | Leu | Asn | Glu | Glu | Gln | Arg | Asn | Ala | Phe | Ile | Gln |
| | | | | 80 | | | | | 85 | | | | | 90 |
| Ser | Leu | Lys | Asp | Asp | Pro | Ser | Gln | Ser | Ala | Asn | Leu | Leu | Ala | Glu |
| | | | | 95 | | | | | 100 | | | | | 105 |
| Ala | Lys | Lys | Leu | Asn | Asp | Ala | Gln | Ala | Pro | Lys | Val | Asp | Asn | Lys |
| | | | | 110 | | | | | 115 | | | | | 120 |
| Phe | Asn | Lys | Glu | Gln | Gln | Asn | Ala | Phe | Tyr | Glu | Ile | Leu | His | Leu |
| | | | | 125 | | | | | 130 | | | | | 135 |
| Pro | Asn | Leu | Asn | Glu | Glu | Gln | Arg | Asn | Ala | Phe | Ile | Gln | Ser | Leu |
| | | | | 140 | | | | | 145 | | | | | 150 |
| Lys | Asp | Asp | Pro | Ser | Gln | Ser | Ala | Asn | Leu | Leu | Ala | Glu | Ala | Lys |
| | | | | 155 | | | | | 160 | | | | | 165 |
| Lys | Leu | Asn | Asp | Ala | Gln | Ala | Pro | Lys | Val | Asp | Asn | Lys | Phe | Asn |
| | | | | 170 | | | | | 175 | | | | | 180 |
| Lys | Glu | Gln | Gln | Asn | Ala | Phe | Tyr | Glu | Ile | Leu | His | Leu | Pro | Asn |
| | | | | 185 | | | | | 190 | | | | | 195 |
| Leu | Asn | Glu | Glu | Gln | Arg | Asn | Ala | Phe | Ile | Gln | Ser | Leu | Lys | Asp |
| | | | | 200 | | | | | 205 | | | | | 210 |
| Asp | Pro | Ser | Gln | Ser | Ala | Asn | Leu | Leu | Ala | Glu | Ala | Lys | Lys | Leu |
| | | | | 215 | | | | | 220 | | | | | 225 |

FIG. 9 (continued)

```
Asn Asp Ala Gln Ala Pro Lys Val Asp Asn Lys Phe Asn Lys Glu
                230                 235                 240

Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro
                260                 265                 270

Ser Gln Ser Ala Asn Leu Leu Ala Glu Ala Lys Lys Leu Asn Asp
                275                 280                 285

Ala Gln Ala Pro Lys His His His His His His Cys Cys Lys
                290                 295                 300

Cys
```

SEQ ID NO: 10
LIENGTH: 391
TYPE: PRT
ORGANISM: Artificial Sequence
OTHER INFORMATION: PentaZ-H

```
Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys Asp Asp Pro Ser Gln Ser Ala Asn Leu Leu
                35                  40                  45

Ala Glu Ala Lys Lys Leu Asn Asp Ala Gln Ala Pro Lys Glu Ala
                50                  55                  60

Gln Lys Gln Lys Glu Gln Arg Gln Ala Ala Glu Glu Leu Ala Asn
                65                  70                  75

Ala Val Asp Asn Lys Phe Asn Lys Glu Gln Gln Asn Ala Phe Tyr
                80                  85                  90

Glu Ile Leu His Leu Pro Asn Leu Asn Glu Glu Gln Arg Asn Ala
                95                  100                 105

Phe Ile Gln Ser Leu Lys Asp Asp Pro Ser Gln Ser Ala Asn Leu
                110                 115                 120

Leu Ala Glu Ala Lys Lys Leu Asn Asp Ala Gln Ala Pro Lys Glu
                125                 130                 135
```

FIG. 9 (continued)

```
Ala Gln Lys Gln Lys Glu Gln Arg Gln Ala Ala Glu Glu Leu Ala
                140                 145                 150

Asn Ala Val Asp Asn Lys Phe Asn Lys Glu Gln Gln Asn Ala Phe
                155                 160                 165

Tyr Glu Ile Leu His Leu Pro Asn Leu Asn Glu Glu Gln Arg Asn
                170                 175                 180

Ala Phe Ile Gln Ser Leu Lys Asp Asp Pro Ser Gln Ser Ala Asn
                185                 190                 195

Leu Leu Ala Glu Ala Lys Lys Leu Asn Asp Ala Gln Ala Pro Lys
                200                 205                 210

Glu Ala Gln Lys Gln Lys Glu Gln Arg Gln Ala Ala Glu Glu Leu
                215                 220                 225

Ala Asn Ala Val Asp Asn Lys Phe Asn Lys Glu Gln Gln Asn Ala
                230                 235                 240

Phe Tyr Glu Ile Leu His Leu Pro Asn Leu Asn Glu Glu Gln Arg
                245                 250                 255

Asn Ala Phe Ile Gln Ser Leu Lys Asp Asp Pro Ser Gln Ser Ala
                260                 265                 270

Asn Leu Leu Ala Glu Ala Lys Lys Leu Asn Asp Ala Gln Ala Pro
                275                 280                 285

Lys Glu Ala Gln Lys Gln Lys Glu Gln Arg Gln Ala Ala Glu Glu
                290                 295                 300

Leu Ala Asn Ala Val Asp Asn Lys Phe Asn Lys Glu Gln Gln Asn
                305                 310                 315

Ala Phe Tyr Glu Ile Leu His Leu Pro Asn Leu Asn Glu Glu Gln
                320                 325                 330

Arg Asn Ala Phe Ile Gln Ser Leu Lys Asp Asp Pro Ser Gln Ser
                335                 340                 345

Ala Asn Leu Leu Ala Glu Ala Lys Lys Leu Asn Asp Ala Gln Ala
                350                 355                 360

Pro Lys Glu Ala Gln Lys Gln Lys Glu Gln Arg Gln Ala Ala Glu
                365                 370                 375

Glu Leu Ala Asn Ala His His His His His His Cys Cys Lys
                380                 385                 390
```

FIG. 9 (continued)

```
Cys

SEQ ID NO: 11
LIENGTH: 301
TYPE: PRT
ORGANISM: Artificial Sequence
OTHER INFORMATION: PentaZD36H Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys His Asp Pro Ser Gln Ser Ala Asn Leu Leu
                35                  40                  45

Ala Glu Ala Lys Lys Leu Asn Asp Ala Gln Ala Pro Lys Val Asp
                50                  55                  60

Asn Lys Phe Asn Lys Glu Gln Gln Asn Ala Phe Tyr Glu Ile Leu
                65                  70                  75

His Leu Pro Asn Leu Asn Glu Glu Gln Arg Asn Ala Phe Ile Gln
                80                  85                  90

Ser Leu Lys His Asp Pro Ser Gln Ser Ala Asn Leu Leu Ala Glu
                95                  100                 105

Ala Lys Lys Leu Asn Asp Ala Gln Ala Pro Lys Val Asp Asn Lys
                110                 115                 120

Phe Asn Lys Glu Gln Gln Asn Ala Phe Tyr Glu Ile Leu His Leu
                125                 130                 135

Pro Asn Leu Asn Glu Glu Gln Arg Asn Ala Phe Ile Gln Ser Leu
                140                 145                 150

Lys His Asp Pro Ser Gln Ser Ala Asn Leu Leu Ala Glu Ala Lys
                155                 160                 165

Lys Leu Asn Asp Ala Gln Ala Pro Lys Val Asp Asn Lys Phe Asn
                170                 175                 180

Lys Glu Gln Gln Asn Ala Phe Tyr Glu Ile Leu His Leu Pro Asn
                185                 190                 195
```

FIG. 9 (continued)

```
Leu Asn Glu Glu Gln Arg Asn Ala Phe Ile Gln Ser Leu Lys His
                200                 205                 210

Asp Pro Ser Gln Ser Ala Asn Leu Leu Ala Glu Ala Lys Lys Leu
                215                 220                 225

Asn Asp Ala Gln Ala Pro Lys Val Asp Asn Lys Phe Asn Lys Glu
                230                 235                 240

Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys His Asp Pro
                260                 265                 270

Ser Gln Ser Ala Asn Leu Leu Ala Glu Ala Lys Lys Leu Asn Asp
                275                 280                 285

Ala Gln Ala Pro Lys His His His His His His Cys Cys Lys
                290                 295                 300

Cys
```

SEQ ID NO: 12
LIENGTH: 243
TYPE: PRT
ORGANISM: Artificial Sequence
OTHER INFORMATION: TetraZ

```
Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys Asp Asp Pro Ser Gln Ser Ala Asn Leu Leu
                35                  40                  45

Ala Glu Ala Lys Lys Leu Asn Asp Ala Gln Ala Pro Lys Val Asp
                50                  55                  60

Asn Lys Phe Asn Lys Glu Gln Gln Asn Ala Phe Tyr Glu Ile Leu
                65                  70                  75

His Leu Pro Asn Leu Asn Glu Glu Gln Arg Asn Ala Phe Ile Gln
                80                  85                  90

Ser Leu Lys Asp Asp Pro Ser Gln Ser Ala Asn Leu Leu Ala Glu
                95                  100                 105
```

FIG. 9 (continued)

```
Ala Lys Lys Leu Asn Asp Ala Gln Ala Pro Lys Val Asp Asn Lys
            110                 115                 120

Phe Asn Lys Glu Gln Gln Asn Ala Phe Tyr Glu Ile Leu His Leu
            125                 130                 135

Pro Asn Leu Asn Glu Glu Gln Arg Asn Ala Phe Ile Gln Ser Leu
            140                 145                 150

Lys Asp Asp Pro Ser Gln Ser Ala Asn Leu Leu Ala Glu Ala Lys
            155                 160                 165

Lys Leu Asn Asp Ala Gln Ala Pro Lys Val Asp Asn Lys Phe Asn
            170                 175                 180

Lys Glu Gln Gln Asn Ala Phe Tyr Glu Ile Leu His Leu Pro Asn
            185                 190                 195

Leu Asn Glu Glu Gln Arg Asn Ala Phe Ile Gln Ser Leu Lys Asp
            200                 205                 210

Asp Pro Ser Gln Ser Ala Asn Leu Leu Ala Glu Ala Lys Lys Leu
            215                 220                 225

Asn Asp Ala Gln Ala Pro Lys His His His His His His Cys
            230                 235                 240

Cys Lys Cys
```

SEQ ID NO: 13
LIENGTH: 397
TYPE: PRT
ORGANISM: Artificial Sequence
OTHER INFORMATION: TetraZ-H

```
Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe
                20                  25                  30

Ile Gln Ser Leu Lys Asp Asp Pro Ser Gln Ser Ala Asn Leu Leu
                35                  40                  45

Ala Glu Ala Lys Lys Leu Asn Asp Ala Gln Ala Pro Lys Glu Ala
                50                  55                  60
```

FIG. 9 (continued)

```
Gln Lys Gln Lys Glu Gln Arg Gln Ala Ala Glu Glu Leu Ala Asn
                65                  70                  75
Ala Val Asp Asn Lys Phe Asn Lys Glu Gln Gln Asn Ala Phe Tyr
                80                  85                  90
Glu Ile Leu His Leu Pro Asn Leu Asn Glu Glu Gln Arg Asn Ala
                95                 100                 105
Phe Ile Gln Ser Leu Lys Asp Asp Pro Ser Gln Ser Ala Asn Leu
               110                 115                 120
Leu Ala Glu Ala Lys Lys Leu Asn Asp Ala Gln Ala Pro Lys Glu
               125                 130                 135
Ala Gln Lys Gln Lys Glu Gln Arg Gln Ala Ala Glu Glu Leu Ala
               140                 145                 150
Asn Ala Val Asp Asn Lys Phe Asn Lys Glu Gln Gln Asn Ala Phe
               155                 160                 165
Tyr Glu Ile Leu His Leu Pro Asn Leu Asn Glu Glu Gln Arg Asn
               170                 175                 180
Ala Phe Ile Gln Ser Leu Lys Asp Asp Pro Ser Gln Ser Ala Asn
               185                 190                 195
Leu Leu Ala Glu Ala Lys Lys Leu Asn Asp Ala Gln Ala Pro Lys
               200                 205                 210
Glu Ala Gln Lys Gln Lys Glu Gln Arg Gln Ala Ala Glu Glu Leu
               215                 220                 225
Ala Asn Ala Val Asp Asn Lys Phe Asn Lys Glu Gln Gln Asn Ala
               230                 235                 240
Phe Tyr Glu Ile Leu His Leu Pro Asn Leu Asn Glu Glu Gln Arg
               245                 250                 255
Asn Ala Phe Ile Gln Ser Leu Lys Asp Asp Pro Ser Gln Ser Ala
               260                 265                 270
Asn Leu Leu Ala Glu Ala Lys Lys Leu Asn Asp Ala Gln Ala Pro
               275                 280                 285
Lys His His His His His His Cys Cys Lys Cys
               290                 295
```

FIG. 9 (continued)

SEQ ID NO: 14
LENGTH: 20
TYPE: PRT
ORGANISM: Homo Sapiens
OTHER INFORMATION: Glucagon Thr Ser Asp Tyr Ser Lys Tyr Leu Asp Ser Arg Arg Ala Gln Asp Phe Val
Gln Trp Leu

SEQ ID NO: 15
LENGTH: 23
TYPE: PRT
ORGANISM: Paramecium tetraurelia
OTHER INFORMATION: Calmodulin Phe Leu Ser Leu Met Ala Arg Lys Met Lys Glu Gln Asp Ser Glu Glu Glu
Leu Ile Glu Ala Phe Lys

SEQ ID NO: 16
LENGTH: 27
TYPE: PRT
ORGANISM: Homo Sapiens
OTHER INFORMATION: Myosin-10

Glu Ile Asp Ser Thr Trp Ser Ala Leu Glu Lys Ala Glu Gln Glu His Ala
Glu Ala Leu Arg Ile Glu Leu Lys Arg Gln

SEQ ID NO: 17
LENGTH: 75
TYPE: PRT
ORGANISM: Homo Sapiens
OTHER INFORMATION: Sumo1

Glu Gly Glu Tyr Ile Lys Leu Lys Val Ile Gly Gln Asp Ser Ser Glu Ile
His Phe Lys Val Lys Met Thr Thr His Leu Lys Lys Leu Lys Glu Ser Tyr
Cys Gln Arg Gln Gly Val Pro Met Asn Ser Leu Arg Phe Leu Phe Glu Gly
Gln Arg Ile Ala Asp Asn His Thr Pro Lys Glu Leu Gly Met Glu Glu Glu
Asp Val Ile Glu Val Tyr Gln

SEQ ID NO: 18
LENGTH: 48
TYPE: PRT
ORGANISM: Homo Sapiens
OTHER INFORMATION: EGF-Like Domain of heregulin-alpha

FIG. 9 (continued)

```
Asn Ser Tyr Pro Gly Cys Pro Ser Ser Tyr Asp Gly Tyr Cys Leu Asn Gly
Gly Val Cys Met His Ile Glu Ser Leu Asp Ser Tyr Thr Cys Asn Cys Val
Ile Gly Tyr Ser Gly Asp Arg Cys Gln Thr Arg Asp Leu Arg
```

SEQ ID NO: 19
LENGTH: 40
TYPE: PRT
ORGANISM: Homo Sapiens
OTHER INFORMATION: UBA domain of Rad23A

```
Ser Glu Tyr Glu Thr Met Leu Thr Glu Ile Met Ser Met Gly Tyr Glu Arg
Glu Arg Val Val Ala Ala Leu Arg Ala Ser Tyr Asn Asn Pro His Arg Ala
Val Glu Tyr Leu Leu Thr
```

SEQ ID NO: 20
TYPE: PRT
ORGANISM: Group G Streptococci
OTHER INFORMATION: B1 or C1 domain

```
Thr Tyr Lys Leu Ile Leu Asn Gly Lys Thr Leu Lys Gly Glu Thr Thr Thr
Glu Ala Val Asp Ala Ala Thr Ala Glu Lys Val Phe Lys Gln Tyr Ala Asn
Asp Asn Gly Val Asp Gly Glu Trp Thr Tyr Asp Asp Ala Thr Lys Thr Phe
Thr Val Thr Glu Lys Pro Glu Val Ile Asp Ala Ser Glu Leu Thr Pro Ala
Val Thr
```

SEQ ID NO: 21
TYPE: PRT
ORGANISM: Group G Streptococci
OTHER INFORMATION: B2 or C2 domain

```
Thr Tyr Lys Leu Val Ile Asn Gly Lys Thr Leu Lys Gly Glu Thr Thr Thr
Lys Ala Val Asp Ala Glu Thr Ala Glu Lys Ala Phe Lys Gln Tyr Ala Asn
Asp Asn Gly Val Asp Gly Val Trp Thr Tyr Asp Asp Ala Thr Lys Thr Phe
Thr Val Thr Glu
```

AFFINITY CHROMATOGRAPHY LIGANDS WITH MILD ELUTION PH

TECHNICAL FIELD

This disclosure relates to chromatography ligands and methods of use thereof.

BACKGROUND

*Staphylococcus* Protein A (SPA) is a surface protein originally found in the cell wall of the bacteria *Staphylococcus aureus*. Because of its immunoglobulin binding capacity, SPA is widely used as a chromatography ligand in monoclonal antibody (i.e. immunoglobulin G or IgG) production in the biotechnological and pharmaceutical industries.

SPA binds to human IgG very tightly. Due to the high affinity, elution of the bound IgG from SPA ligands requires a harsh acidic condition, e.g., pH 3. However, in strong acidic conditions, the structure of IgG is partially denatured, which often leads to aggregation and precipitation of the antibody. It has been shown that at about pH 3, IgG structure and dimension shifted dramatically (Pete Gagnon, et. al. Conformational plasticity of IgG during protein A affinity chromatography. Journal of Chromatography A, 1433 (2016) 98-105). Thus, the denaturation can be detrimental to antibody production. Therefore, there is a need to develop chromatography ligands that would allow antibodies to be eluted at a higher pH, which would minimize structural damage of the antibody molecules.

SUMMARY

This disclosure relates to chromatography ligands and methods of use thereof.

In one aspect, the disclosure relates to polypeptides having at least two binding units and at least one spacer domain, wherein every two neighboring binding units are separated by at least one spacer domain, and each binding unit comprises one or two immunoglobulin binding domains.

In some embodiments, the spacer domain is not a random coil or a disordered loop at pH about 4.5 to about 7. In some embodiments, every two neighboring binding units are separated by one spacer domain. The immunoglobulin binding domain can be a *Staphylococcal* Protein A (SPA) immunoglobulin binding domain or functional variants thereof. In some embodiments, the immunoglobulin binding domain is domain A of SPA, domain B of SPA, domain C of SPA, domain D of SPA, domain E of SPA, domain Z, domain $Z_{D36H}$, or functional variants thereof.

In some embodiments, the immunoglobulin binding domain has a sequence that is at least 90% identical to domain Z, and the immunoglobulin binding domain can bind to the Fc region of an immunoglobulin.

In some embodiments, the immunoglobulin binding domain is a *Streptococcal* Protein G (SPG) immunoglobulin binding domain, or functional variants thereof.

In some embodiments, at least one immunoglobulin binding domain is a SPA immunoglobulin binding domain, and at least one immunoglobulin binding domain is a SPG immunoglobulin binding domain.

In some embodiments, the spacer domain comprises an alpha helix or a helix bundle. The spacer domain can be a L9 connecting helix, or functional variants thereof. The space domain can also be a domain of glucagon (SEQ ID NO: 14), a connecting helix of calmodulin (SEQ ID NO: 15), a single alpha-helix domain (SAH) of Myosin-10 (SEQ ID NO: 16), a Sumo domain (SEQ ID NO: 17), an EGF domain (SEQ ID NO: 18), a ubiquitin-associated (UBA) domain of Rad23A (SEQ ID NO: 19), an IgG-like domains, a lysozyme, or functional variants thereof.

In some embodiments, the maximum diameter of the spacer domain is less than 100 Å.

In some embodiments, the spacer domain has fewer than 80 amino acid residues.

In some embodiments, the polypeptide has a sequence as defined by Formula II:

$$S_{0-1}(R_{1-2}S)_n R_{0-2} \quad \text{(Formula II)}$$

wherein
R represents an immunoglobulin binding domain;
S represents a spacer domain;
n is an integer, indicating the number of repeating units in the protein, and n can be equal to 1 or larger than 1.

In some embodiments, the polypeptide has a sequence as defined by Formula III.

$$\text{RSRSRSRS} \quad \text{(Formula III)}.$$

In some embodiments, the polypeptide has a sequence as defined by Formula IV:

$$\text{RR—S—RR—S—RR—S} \quad \text{(Formula IV)}$$

In some embodiments, the polypeptide further comprises a poly-His tag and/or a cysteine residue for immobilization.

In one aspect, the disclosure provides vectors comprising a polynucleotide encoding any polypeptide as described herein.

In another aspect, the disclosure also provides chromatography ligands comprising any polypeptide as described herein.

In some embodiments, the chromatography ligand has a recovery yield over 60% with elution pH at 4.7 or higher.

In some embodiments, the chromatography ligand has a recovery yield over 80% with elution pH at 4.7 or higher.

In some embodiments, the chromatography ligand is immobilized on a matrix. The matrix can be in the form of beans or in the form of a membrane.

The disclosure also relates to methods of purifying immunoglobulins. The methods include the steps of contacting the chromatography ligand of claim 23 with a solution comprising immunoglobulins; washing the chromatography ligand with a first buffer; and eluting the immunoglobulins with a second buffer having a selected pH, wherein the selected pH is greater than 4.0. In some embodiments, the selected pH is 4.7. In some embodiments, the recovery yield for the eluted immunoglobulins is greater than 90%.

The disclosure also provides methods of purifying immunoglobulins. The methods include the steps of contacting the chromatography ligand of claim 23 with a solution comprising immunoglobulins; washing the chromatography ligand with a buffer, wherein the buffer has a linear pH gradient; and collecting immunoglobulins at a selected pH. In some embodiments, the linear pH gradient is from about pH 8.0 to about pH 3.0. In some embodiments, the selected pH is from about 6.0 to about 4.0. In some embodiments, the recovery yield for the eluted immunoglobulins is greater than 90%.

As used herein, the term "binding unit" refers to a region in a polypeptide that can bind to immunoglobulins. Each binding unit has one or two immunoglobulin binding domains.

As used herein, the term "two neighboring binding units" refers to two binding units that are close to each other, and they are separated by spacer domains.

As used herein, the term "immunoglobulin binding domain" refers to a domain that can bind to a constant region of immunoglobulins (e.g., Fc of IgG).

As used herein, the term "protein domain" or "domain" refers to a structurally stable unit or region of a protein. Unlike a random coil or a disordered loop, a domain has a stable and recognizable three-dimensional structure in non-denaturing conditions.

As used herein, the term "spacer domain" refers to a protein domain that separates two domains (e.g., immunoglobulins binding domains). A spacer domain is not a random coil or a disordered loop.

As used herein, the term "Protein A immunoglobulin binding domain" or "SPA immunoglobulin binding domain" refer to an immunoglobulin binding domain of *Staphylococcus* Protein A (e.g., domains B, C, A, E, D), or the functional variants thereof (e.g., domain Z, domain $Z_{D36H}$).

As used herein, the term "Protein G immunoglobulin binding domain" or "SPG immunoglobulin binding domain" refer to an immunoglobulin binding domain of *Staphylococcus* Protein G, or the functional variants thereof.

As used herein, the term "ligand" refers to a substance or molecule that specifically interacts or binds to another molecule.

As used herein, the term "affinity ligand" refers to a molecule which has specific non-covalent binding capability to other molecules.

As used herein, the term "affinity chromatography" refers to chromatography using affinity ligands to bind and purify target molecules.

As used herein, the term "elution" refers to the release of a bound molecule from an affinity ligand.

As used herein, the term "Fc-binding protein" or "Fc-binding domain" refers to a polypeptide capable of binding to the Fragment Crystallizable (FC) region of an antibody. In some embodiments, the Fc-binding protein or Fc-binding domain can be, e.g., Protein A, Protein G, or any fragments or fusion proteins thereof that have the binding property.

As used herein, the term "functional variant" or "variant" of a protein or a protein domain refers to a variant protein or a variant protein domain, which retains essentially similar function of the protein or the protein domain (e.g., bind to Fc, effectively separate immunoglobulin binding domains). In some embodiments, the sequence of the functional variant of a protein or a protein domain has a sequence that is at least 70%, 80%, 90%, 95%, 96%, 97%, 98%, 99% identical to the protein or the protein domain.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows the sequence alignment of *Staphylococcus* Protein A (SPA) IgG binding domain B (SEQ ID NO: 1), domain C (SEQ ID NO: 2), domain A (SEQ ID NO: 3), domain D (SEQ ID NO: 4), domain E (SEQ ID NO: 5), domain Z (SEQ ID NO: 6), and domain Z variant $Z_{D36H}$ (SEQ ID NO: 7). The mutated residues in Z and $Z_{D36H}$ that are related to domain B are shown in frames.

FIG. 2 is a diagram showing the Tri Z—H, Tetra Z—H, Penta Z—H, and Hexa Z—H IgG affinity ligands. IgG binding domains are represented by ovals. Spacer domains, which are represented by diamonds, separate IgG binding domains. The affinity ligands can be coupled to a solid matrix in a single attachment manner.

FIG. 6 is a graph showing pH gradient elution profile for PentaZ-H, PentaZ and $PentaZ_{D56H}$ agarose resins packed in 1-ml column. The pH values corresponding to the center of elution peaks for PentaZ-H, PentaZ and $PentaZ_{D56H}$ are pH 4.91, pH 4.28 and pH 3.86, respectively.

FIG. 7 is graph showing pH step-wise elution profile for PentaZ-H agarose resin packed in a 1-ml column.

FIG. 9 lists the sequences for SEQ ID NOs: 1-21.

DETAILED DESCRIPTION

Figure 3:
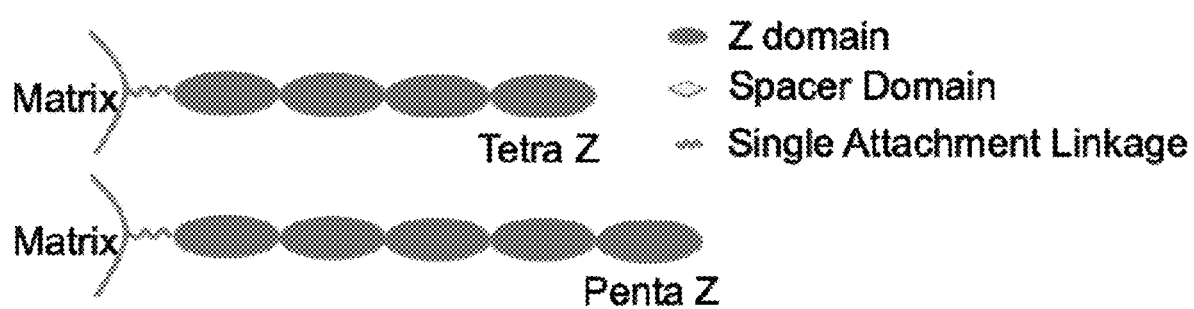
FIG. 3 is a diagram showing classic IgG affinity ligands Tetra Z and Penta Z. In these affinity ligands, 4-5 Z domains are connected in series without any spacer domains.

*Staphylococcus* Protein A is a surface protein originally found in the cell wall of the bacteria *Staphylococcus aureus*. It is encoded by the spa gene in the bacteria. SPA can bind to the Fc region of immunoglobulin (e.g., immunoglobulin G or IgG), impairing phagocytosis of the bacteria by immune cells. Because of its immunoglobulin binding capacity, SPA can be used in affinity chromatography for antibody purification. In fact, Protein A affinity chromatography is wildly used in monoclonal antibody production in the biotechnological and pharmaceutical industry.

SPA has 5 homologous IgG binding domains, which are designated as E, D, A, B, and C (sequences are provided FIG. 1). Each domain has similar IgG binding capability. However, due to their different thermostabilities, only Domains B and C and their functional variants are widely used in monoclonal antibody purification industry. A single amino acid mutation G29A (i.e. Glycine residue at position 29 is substituted to Alanine) makes Domain B resistant to treatment with sodium hydroxide (NaOH) (Bjorn Nilsson, et. al. A synthetic IgG-binding domain based on *staphylococcal* protein A. Protein Engineering vol. 1 no.2 pp. 107-113, 1987). This modified domain B is usually called domain Z. The sequence of domain Z is shown in FIG. 1. Domain C, which is also resistant to NaOH treatment, is also commonly used in antibody purification. Domain C and functional fragments or variants thereof are described, e.g., in U.S. Pat. No. 8,329,860, which is incorporated by reference in its entirety.

The recombinant domain B, domain Z, domain C or their functional variants can be used as chromatographic ligands. They are usually constructed in multiple tandem repeats. Most commercially available SPA ligands have 4 or 5 repeating domains in series, and each ligand can accommodate about 2 IgG molecules in solution. Each IgG binding domain of SPA has a compact 3-helical structure with only a few non-helical residues at the ends. In both native SPA and the commercial SPA ligands (e.g., MABSELECT™ or MABSELECT SURE™ from GE Healthcare), the multimeric IgG binding domains are connected continuously without additional linking sequences in between the binding domains (see, e.g., SEQ ID NOs: 9, 11, and 12). Some of the commercial ligands are described, e.g., in U.S. Pat. No. 8,329,860 B2, which is incorporated by reference in its entirety.

The native SPA binds very tightly with human IgG1, IgG2 and IgG4 with affinity around Kd=10 nM. The engineered Protein A with 4 or 5 tandem domains of B, C or Z exhibits similar binding affinity with IgGs. Due to the high affinity, elution of the bound IgG from SPA ligands requires harsh acidic conditions, e.g., pH 3. In fact, elution buffers around pH 3 are widely used for IgG elution in production of monoclonal antibodies in both industry and research areas. However, in strong acidic conditions, the structure of IgG is partially denatured. It has been shown that at about pH 3, IgG structure and dimension shifted dramatically (Pete Gagnon, et. al. Conformational plasticity of IgG during protein A affinity chromatography. Journal of Chromatography A, 1433 (2016) 98-105). The denaturation can be detrimental to some IgG molecules. One consequence of the acidic denaturation is protein precipitation, which results the loss of the IgG molecules. The second consequence of the acidic denaturation is the formation of soluble aggregates, which are toxic to human being. Intriguingly, the IgG precipitation and aggregation are often related to Protein A chromatography. The interaction and disassociation with Protein A may contribute to the structural damage of the IgG molecules. It is not uncommon to see over 20% of antibody aggregation in modem therapeutic monoclonal antibody production using Protein A chromatography. However, it was also shown that at about pH 4.7 or above, IgG structure can be maintained unchanged. The impact of pH on antibody structure is described, e.g., in Ramil F. Latypov, et. al. Elucidation of acid-induced unfolding and aggregation of human immunoglobulin IgG1 and IgG2 Fc. J Biol Chem. 2012 Jan 6;287(2):1381-96, which is incorporated by reference in its entirety. Therefore, it is more desirable to elute the bound IgG from Protein A media at pH 4.7 or above.

One way to improve the elution pH is to find residues that affect IgG dissociation. Histidine scanning methods can be used to identify residues affecting the elution pH. By using these methods, it has been determined that substitution of Asp36 to His36 and/or Gln9 to His9 will significantly increase the elution around pH 4.5. Histidine scanning methods and substitutions are described, e.g., in U.S. Pat. No. 8,329,860, which is incorporated by reference in its entirety. Another set of mutations (H18S, N28A) can also lead to milder elution conditions, e.g. pH 3.5-4.5. These mutations are described, e.g., in Timothy M. Pabst, et. al. Engineering of novel Staphylococcal Protein A ligands to enable milder elution pH and high dynamic binding capacity. Journal of Chromatography A, 1362 (2014) 180-185; and US 20130274451 A1; each of which is incorporated by reference in its entirety. However, the elution peaks of those SPA mutants (D36H, G9H, H18S, N28A) with milder elution pH are all much broader than the parent proteins, indicating a sluggish elution profile and lower purification yield. Shinya Honda et. al. published another patent application that described a method to add a very long linker between two SPG IgG domains (US 20160280744 A1). The described linker was a random coil with a length of at least 80-240 angstroms. As a result, the elution peak was much broader, indicating non-specific binding, than the parental SPG protein according to the published data.

Another way to achieve the same goal for higher pH elution is to change the structure of IgG Binding domain of SPA. Sophia Hober et. al. found that changing a few residues at one of the loops on Protein A would bring the IgG elution above pH 3.5-pH 4.0 (Susanne Gülich, et. al. Protein engineering of an IgG-binding domain allows milder elution conditions during affinity chromatograph. Journal of Biotechnology 76 (2000) 233-244). Xia H. F. et. al. inserted a 6-glycine linker into one of the Protein A loop to bring up the elution pH above 4.0 (Hai-Feng Xia, et. al. *Molecular Modification of* Protein A to Improve the Elution pH and Alkali Resistance in Affinity Chromatography. Applied Biochemistry and Biotechnology April 2014, Volume 172, Issue 8, pp 4002-4012). However, those structural changes of SPA all result reduced thermostability of the protein or lower expression of the protein.

The present disclosure is based, in part, on the observation that each IgG binding domain of SPA may have a secondary minor FC binding site besides the well-known major FC binding site. In the situation of the tandem connection of IgG binding domains in the native SPA and the commercial SPA variants, a secondary interaction from one IgG binding domain can occur when the adjacent IgG binding domain binds to the dominant FC site. The major and secondary interactions contribute to the extreme high affinity between SPA and IgG due to cooperative effects. That is consistent with the fact that multimeric SPA elution peaks typically are skewed with a trailing tail, indicating a complex multi-site binding model. As illustrated in the examples, the potential secondary binding interaction can be eliminated if the two adjacent IgG binding domains (e.g., SPA immunoglobulin binding domains, SPA immunoglobulin binding domain variants, or SPG immunoglobulin binding domains) are physically separately. A structurally stable domain, which does not interfere with the function of the IgG binding domains, can be inserted as a spacer between the two adjacent IgG binding domains. The spaced immunoglobulin binding domains can have better binding and elution kinetics for immunoglobulins without sacrificing their NaOH resistance.

Immunoglobulin Binding Domains

This disclosure provides chromatography ligands comprising immunoglobulin binding domains. The term "immunoglobulin binding domain" refers to a domain that can bind to a constant region of immunoglobulins.

The immunoglobulin binding domain in the chromatography ligands can be any immunoglobulin binding domain as described herein. For example, the immunoglobulin binding domain can be domains B, C, A, E, D derived from *Staphylococcus* Protein A, or their variants thereof. The immunoglobulin binding domains can also be domain Z or the variants thereof. The domain Z is a functional variant of domain B of Protein A. Domain Z has a 3-helix bundle, which has about 58 amino acids. In some embodiments, domain Z can have one or more of the mutations D36H, G9H, H18S, N23T, F30A, or N28A. In some embodiments, a glycine link (e.g., six glycine residues) can be inserted into the second loop of Z domain (Z (6G)). Z(6G), N23T, F30A are described, e.g., in Hai-Feng Xia, et. al. Molecular Modification of Protein A to Improve the Elution pH and Alkali Resistance in Affinity Chromatography, Applied Biochemistry and Biotechnology April 2014, Volume 172, Issue 8, pp 4002-4012, which is incorporated by reference in its entirety.

In some embodiments, the immunoglobulin binding domain can be an immunoglobulin binding domain in *Streptococcal* Protein G (SPG). Protein G is an immunoglobulin-binding protein expressed in *Streptococcal* bacteria. It is similar to Protein A but it has differing binding specificities. In some cases, the affinity ligands are based on SPG immunoglobulin binding domains, e.g., B1, C1, B2, or C2 depending on the nomenclatures in different literatures. The amino acid sequence for B1/C1 is SEQ ID NO: 20 and the amino acid sequence for B2/C2 is SEQ ID NO: 21. The elution pH of these affinity ligands (without spacer domains) can be in the range of pH 3.5-4.0. SPG immunoglobulin binding domains and their variants are described, e.g., in US 20160280744, which is incorporated by reference in its entirety.

In some embodiments, the immunoglobulin binding domain is an IgG binding domain.

As used herein, a variant immunoglobulin binding domain can be a peptide that has a sequence that is at least 70%, 80%, 90%, 95%, 96%, 97%, 98%, 99% identical to an immunoglobulin binding domains described in this disclosure (e.g., domains B, C, A, E, D, Z, $Z_{D36H}$, or Protein G immunoglobulin binding domain(s)).

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Spacer Domains

As discussed above, this disclosure is based, in part, on the observation that each immunoglobulin binding domain of SPA may have a secondary Fc binding site besides the well-known major Fc binding site. The secondary interaction occurs when the adjacent immunoglobulin binding domain binds to the dominant Fc site. The major and secondary interactions contribute to the extreme high affinity between SPA and IgG due to cooperative effects. In order to eliminate the secondary binding, the neighboring immunoglobulin binding domains can be separated by a spacer domain.

Therefore, the spacer domain needs to be structurally stable and have a defined structure to separate immunoglobulin binding domains. In some cases, the spacer domain can be a structurally stable protein domain, which has a folded three dimensional structure in aqueous solution. The spacer domain can physically separate neighboring immunoglobulin binding domains and serve as a spacer. In some embodiments, the spacer domain has more than 5, 6, 7, 8, 9, 10, 15, 20, 30, or 40 amino acid residues.

As random coils and disordered loops do not have a defined structure in the solution, and cannot effectively separate immunoglobulin binding domains, thus in some embodiments, the spacer domain is not a random coil or a disordered loop. In some embodiments, the spacer domain is not a random coil or a disordered loop at any elution pH described herein (e.g., about 3 to about 7, about 4 to about 7, about 4.5 to about 7).

One important aspect of the spacer domain is its structural stability. The structural stability refers to a well-defined tertiary structure under an appropriate range of conditions including pH, ionic strength, and buffer components in an aqueous solution for chromatography. In some embodiments, the structural stability also means the core of the spacer domain does not form a random coil structure in solution under a condition wherein the affinity ligand binds antibodies. The purpose of the spacer domain is to effectively keep some distance between the neighboring immunoglobulin domains.

In contrast, adding a flexible polypeptide linker between two protein domains is a common method for recombinant expression of a fusion protein or a chimeric protein. The linker is typically designed to be flexible, e.g. a mixture of Gly and Ser residues. These linkers usually cannot prevent the flanking domains from contacting with each other in a solution.

In some embodiments, the spacer domain is a small protein domain, which is about the same size as an immunoglobulin binding domain (e.g. Z domain). In some embodiments, the size of the S domain is similar or larger than a SPA immunoglobulin binding domain. According to crystallographic and NMR studies, the length of a Protein A immunoglobulin binding domain (including domain B, domain C, domain D, domain E, domain A, domain Z or any functional variant) is about 20-30 Å. Therefore, in some embodiments, the length or diameter (e.g., maximum diameter) of a spacer domain can be from about 10 Å to about 60 Å, from about 15 Å to about 45 Å, or from about 20 Å to about 30 Å. In some embodiment, the length or diameter (e.g., maximum diameter) of a spacer domain is less than 100 Å, 90 Å, 80 Å, 70 Å, 60 Å, 50 Å, 40 Å, 30 Å, or 20 Å.

In some embodiments, the spacer domain is water soluble. In these cases, the amino acids that are exposed on the surface of spacer domain are preferably hydrophilic.

In some embodiments, the spacer domain can survive in strong acidic and strong basic conditions, thus have structural stability at low and high pH conditions. In some embodiments, the spacer domain can be easily re-folded to appropriate structure in neutral conditions after being denatured in extreme conditions (e.g., strong basic or acid solutions).

In some embodiments, the spacer domain comprises or consists of an alpha helix structure (e.g., SEQ ID NOs: 8, 15, or 16). The alpha helix can contain about 8 to 32 amino acids, which can form about 2 to 8 helical turns, and ranges from about 10 Å to about 45 Å in length. In some cases, the alpha helix contains about 12 to 24 amino acids, which can form about 3 to 6 helical turns and ranges from about 16 Å to about 35 Å in length.

In some embodiments, the spacer domain is a single alpha helical domain. The single alpha helical domain is a good choice for spacer domain for several reasons. First, single alpha helical domains are the smallest domains that have stable structure. Second, they can easily be refolded after acid or base denaturing during purification process. Third, they have perfect N—C orientation to be integrated into the ligand. Finally, their size/length can be easily controlled as desired.

In some embodiments, the spacer domain can be the central connecting helix of ribosomal protein L9 from *B. stearothermophilus* (SEQ ID NO: 8). The L9 connecting helix, is a stable and soluble helix, which is conserved in many species. The structure of the L9 connecting helix is described, e.g., in David W. Hoffman, et. al. Crystal structure of prokaryotic ribosomal protein L9: a bi-lobed RNA-bindingprotein. The EMBO Journal vol. 13 no.1 pp. 205-212, 1994, which is incorporated by reference in its entirety.

In some embodiments, the helix domain can also have a predominantly hydrophilic surface. In some cases, greater than 50%, 60%, 70%, 80%, 90%, 95% or all of the amino acids that are exposed on the surface of the helix domain are hydrophilic. In some embodiments, hydrophobic areas or patches on the surface of the helix domain are avoided.

In some embodiments, the spacer domain can comprise or consists of a beta sheet (β-sheet). The β-sheet is a common motif of regular secondary structure in proteins. It is made of beta strands (also β-strand), which are connected laterally by at least two or three backbone hydrogen bonds, forming a generally twisted, pleated sheet.

In some embodiments, the spacer domain can be a helical segment of glucagon (amino acids 7-26 of glucagon; SEQ ID NO: 14), connecting helix of calmodulin (amino acids 68-90 of calmodulin; SEQ ID NO: 15), or single alpha-helix domain (SAH) from Myosin-10 (amino acids 813-909 of Myosin-10; SEQ ID NO: 16).

In some embodiments, the spacer domain is a small protein such as a Sumo domain (alpha helix and beta sheet; e.g., SEQ ID NO: 17), an EGF domain (beta sheet; e.g., SEQ ID NO: 18) or an ubiquitin-associated (UBA) domain of Rad23A (e.g., SEQ ID NO: 19).

In some embodiments, the spacer domain can be a peptide that has a sequence that is at least 70%, 80%, 90%, 95%, 96%, 97%, 98%, 99% identical to any spacer domain described in this disclosure (e.g., SEQ ID NOs: 8, 14-19).

In some embodiments, the spacer domain is a non-IgG binding domain. In some cases, the spacer domain does not have affinity to immunoglobulins or IgG. It does not affect the structural stability of the adjacent immunoglobulin binding domains and does not interfere with the refolding of the immunoglobulin binding domains after NaOH Cleaning in Place (CIP).

In some embodiments, the spacer domain does not interact with the neighboring immunoglobulin binding domains under physiological conditions or denaturing conditions (e.g., the spacer domain will not bind to the neighboring immunoglobulin binding domains, and will not block the binding between immunoglobulin binding domains and IgG). The spacer domain does not cause aggregation or denaturing of the immunoglobulin binding domains.

In some embodiments, the spacer domain is a folded protein domain, is a protein domain with three-dimensional structure, is a piece of alpha helix, is a helix bundle, is a beta-structure protein, is a mixed alpha-beta structure protein, or is a globular protein. In some cases, the spacer domain has no immunoglobulin binding affinity, is water soluble, is not a random coil in solution, is not a disordered loop in solution, and/or does not interfere with the function of Immunoglobulin binding domains.

Chromatography Ligands

In one aspect, the chromatography ligands can be peptides, having at least two binding units and at least one spacer domain. A binding unit is a structural element of a polypeptide and it has one or two immunoglobulin binding domains. The polypeptides can have multiple binding units. Every two neighboring binding units are separated by at least one spacer domain. In some embodiments, the polypeptides have at least two immunoglobulin binding domains and at least one spacer domain, wherein every two neighboring immunoglobulin binding domains are separated by at least one spacer domain. In some embodiments, the polypeptides are fusion polypeptides.

The chromatography ligands can have 2, 3, 4, 5, 6, 7, 8 or more than 8 binding units. Each binding unit can have one or two immunoglobulin binding domains. Three or more than three consecutively connected immunoglobulin binding domains is usually not favorable. This is because based on structural studies, each IgG heavy chain has one major SPA binding site, and secondary or minor binding sites on an IgG heavy chain may also be present. Due to steric hindrance of large immunoglobulin molecules such as IgGs, three or more than three tandem SPA domains that are consecutively connected are much more likely to interact with the secondary or minor sites of the immunoglobulins (e.g. IgG). This interaction will result higher binding affinity, and in some cases, is not desirable (make it harder to elute immunoglobulins).

In some embodiments, the chromatography ligands can have multiple immunoglobulin binding domains, which are spatially separated by spacer domains.

In some embodiments, the chromatography ligands can have additional residues or components, e.g. a Cysteine residues or a poly-His tag, that can be used, e.g., for linking the chromatography ligand to a support matrix, solid surface or bead. Cysteine residues can be used for immobilization. Poly-His tags can be used for purifying chromatography ligands. Cysteine residues and poly-His tags are described, e.g., in Kimple, Michelle E., and John Sondek. "Overview of affinity tags for protein purification." Current Protocols in Protein Science (2004): 9-9; Magdeldin, Sameh, and Annette Moser. "Affinity chromatography: Principles and applications." S. Magdeldin, InTech, Croatia (2012): 1-28; each of which is incorporated by reference in its entirety.

In some embodiments, the chromatography ligands have the structure as defined by the following formulas:

$$XS_{0-1}(R_{1-2}S)_nR_{0-2}Y \quad \text{(Formula I)}$$

$$S_{0-1}(R_{1-2}S)_nR_{0-2} \quad \text{(Formula II)}$$

$$RSRSRSRS \quad \text{(Formula III)}.$$

$$RRSRRSRRS \quad \text{(Formula IV)}$$

$$RSRSRSRSRS \quad \text{(Formula V)}$$

wherein

R represents an immunoglobulin binding domain (e.g., SPA immunoglobulin binding domain, or SPG immunoglobulin binding domain);

S represents a spacer domain;

n is an integer, indicating the number of repeating units in the protein. The repeating unit is a structural element of the polypeptide and has the structure ($R_{1-2}S$). The ligand can have multiple repeating units. n can be equal to 1 or larger than 1. In some embodiments, n is 1, 2, 3, 4, 5, 6, 7, 8, 9, 10, 11, 12, 13, 14, or 15. In some embodiments, n is less than 15, less than 10, less than 5.

X represents additional residues or components, e.g. Cysteine residues or poly-His tag;

Y represents additional residues or components, e.g. Cysteine residues or poly-His tag;

Under-script numbers represent a range of possible units, e.g. 0-1 meaning 0 or 1 unit.

A spacer domain, due to its structural rigidity, physically separates the two neighboring immunoglobulin binding domains in solution. As used herein, the term "neighboring immunoglobulin binding domains" refers to two immunoglobulin binding domains that are close to each other, and they can be separated by spacer domains.

In some embodiments, the affinity ligand is a chimeric fusion protein comprising IgG binding domains (as an immunoglobulin binding domain) and non-IgG binding domains (as a spacer domain). In some embodiments, the fusion protein contains multiple copies of IgG binding domains from Protein A. In some embodiments, the fusion protein contains multiple copies of non-IgG binding domains.

In some embodiments, the fusion protein contains two or more copies of an identical immunoglobulin binding domain or its functional variant, e.g., multiple Z domains. In some embodiments, the fusion protein contains various IgG binding domains from SPA and SPG, e.g. "Z-S-B1-S" wherein Z represents a SPA immunoglobulin binding domain, B1 represents a SPG immunoglobulin binding domain, and S represents a spacer domain.

In some embodiments, each immunoglobulin binding domain is immediately followed by a spacer domain S, e.g. "RS—RS—RS—RS". In some embodiments, every two immunoglobulin binding domains are followed by a spacer domain S, e.g. "RR—S—RR—S—RR—S."

In some embodiments, the affinity ligands have a greatly improved elution profile with significantly elevated elution pH and narrower elution peak. As discussed above, the structurally rigid spacer domain physically effectively separates immunoglobulin binding domains. Thus, in some cases, the secondary binding provided by adjacent immunoglobulin binding domains in native Protein A and in the classic multimeric recombinant SPA variants is diminished due to the presence of the spacer domain between the immunoglobulin binding domains. Thus, as described in this disclosure, inserting a rigid spacer domain between the neighboring immunoglobulin binding domains in the affinity ligands reduces the acidity requirement for elution.

Thus, the affinity ligands can have higher elution pH for bound immunoglobulins (e.g., IgG). In some embodiments, the elution pH is in the range of pH 4.0 to pH 6.0 with a recovery yield over 70%, 80%, 90%, 95%, 95%, 96%, 97%, 98%, or 99%. In some embodiments, the elution pH is in the range of pH 4.5 to pH 6.0 with a recovery yield over 70%, 80%, 90%, 95%, 95%, 96%, 97%, 98%, or 99%. In some embodiments, the elution pH is in the range of pH 4.5 to pH 5.5 for immunoglobulins with a recovery yield over 90%, 95%, 95%, 96%, 97%, 98%, or 99%. In some embodiments, the elution pH is in the range of pH 4.7-pH 5.0 with a recovery yield over 90%, 95%, 95%, 96%, 97%, 98%, or 99%. As used herein, the recovery yield refers to the percentage of immunoglobulins (e.g., IgG) that can be eluted at certain conditions (e.g., elution pH in the range of pH 4.5 to pH 5.5) out of the total amount immunoglobulins that can be eluted from chromatography. In some embodiments, the total amount immunoglobulins that can be eluted from chromatography is determined by the total amount of immunoglobulins that can be eluted at pH 2-3.

In some embodiments, the affinity ligands that allows bound antibodies to be eluted above pH 4.0, above pH 4.1, above pH 4.2, above pH 4.3, above pH 4.4, above pH 4.5, above pH 4.6, above pH 4.7, above pH 4.8, above pH 4.9, above pH 5.0, above pH 5.1, above pH 5.2, above pH 5.3, above pH 5.4, above pH 5.5, above pH 5.6, above pH 5.7, above pH 5.8, above pH 5.9, above pH 6.0, above pH 6.1, above pH 6.2, above pH 6.3, above pH 6.4, or above pH 6.5. In some embodiments, the maximum elution pH is 6.0, 6.1, 6.2, 6.3, 6.4, or 6.5.

The recovery yield can be above 85%, 86%, 87%, 88%, 89%, 90%, 91%, 92%, 93%, 94%, 95%, 96%, 97%, 98%, or 99%. In some embodiments, the recovery yield is 85-99%, 90%-99%, or 95-99%.

In some embodiments, adding the structurally stable spacer domains to the affinity ligands does not significantly lower the expression yield or decrease the solubility of the affinity ligands.

The affinity ligands described herein can be expressed in a protein expression system such as *Pichia pastoris, E. coli* or any other appropriate expression system known in the art. In some embodiments, the expressed affinity ligands can be purified by using chromatography techniques such as ionic exchanges, affinity, size exclusion and gel filtration. In some embodiments, the purified protein is buffer-exchanged to an amine-free and reducing-agent free buffer, which has about neutral pH. In some embodiments, the purified protein can be concentrated or diluted to an appropriate concentration, which is suitable for coupling to a solid support.

Furthermore, most commercial SPA ligands contain 4 or 5 IgG-binding domains. If the spacer or linker region between the IgG domains is too big (i.e. too many amino acids or too long size-wise), the entire ligand will become too big, thus becoming too complex for synthesis/expression or too difficult for refolding after NaOH cleaning. Thus, in some embodiments, the spacer domain has less than 90, 80, 60, 50, 40, or 30 amino acid residues. In some embodiments, the length or diameter (e.g., maximum diameter when it is properly folded) of a spacer domain can be less than 60 Å, 50 Å, 40 Å, 30 Å, or 20 Å.

Chromatography Matrix

The disclosure also provides a chromatography matrix for affinity separation of antibodies. The matrix can include affinity ligands that are covalently coupled to a solid support. The affinity ligands can be any affinity ligands described herein.

The solid support of the matrix can be made of any kind of suitable materials including polysaccharides (e.g., agarose, cellulose, starch, dextran), organic polymers (e.g., polyacrylamide, polyvinyl alcohol, polyhydroxyalkyl methacrylates) or inorganic aggregates (e.g., silica). The chromatography matrix can be in the form of beads (e.g., substantially spherical particles), a membrane, or monolithic gel. In some embodiments, the affinity ligands described herein can be covalently coupled to the matrix support in a single attachment style (e.g., with one attachment point). In some other cases, the affinity ligands can be covalently coupled to the support with multiple attachment points.

In some embodiments, the chromatography matrix coupled with the affinity ligands can be used in single-use style, which means the matrix is disposed after use without a CIP and validation procedures.

In some embodiments, the chromatography ligands have excellent NaOH resistance, which is required for multiple round of CIP (Cleaning in Place). Thus, in some embodiments, the chromatography matrix coupled with the affinity ligands can be used in multiple cycles with CIP (i.e. cleaning with 0.1-0.5 M NaOH) treatment. The CIP treatment can clean the affinity ligands.

Chromatography Process

The chromatography matrix can be used to purify immunoglobulins, e.g., IgG. The chromatography process relates to affinity chromatography technique, which is known in the art. Thus, this disclosure also provides chromatography processes, wherein a target immunoglobulin is separated from a solution by binding to the chromatography matrix. As a skilled person in the field will easily understand, a solution denoted as an eluent is needed to pass through the affinity matrix to release or elute the bound protein on the matrix. In the case of Protein A chromatography (e.g., HiTrap Protein A HP), the bound antibody (e.g., IgG) on the matrix is commonly eluted by passing an strong acidic solution with pH around 3.0. Such strong acidic condition often causes antibody denaturation and aggregation. In contrast, the affinity ligands described in this disclosure can have higher elution pH for bound immunoglobulins. Thus, in some embodiments, the bound antibody (e.g., IgG) on the matrix is eluted by a solution with appropriate elution pH as described in this disclosure (e.g., pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, or pH 6.5, or in the range of pH 4.0 to pH 6.0).

In some embodiments, the chromatography ligands described herein allows the bound antibodies (e.g., IgG) to be eluted in relatively mild conditions, e.g., above pH 4.0, above pH 4.1, above pH 4.2, above pH 4.3, above pH 4.4, above pH 4.5, above pH 4.6, above pH 4.7, above pH 4.8, above pH 4.9, above pH 5.0, above pH 5.1, above pH 5.2, above pH 5.3, above pH 5.4, above pH 5.5, above pH 5.6, above pH 5.7, above pH 5.8, above pH 5.9, or above pH 6.0.

In some embodiments, the antibody is first bound to the affinity matrix. Solutions with a roughly linear gradient of pH from about pH 8.0 to about pH 3.0 is used to elute the bound antibody. Thus, in some embodiments the bound antibody (e.g., IgG) on the matrix are collected when the elution pH is in any appropriate pH ranges that are described in this disclosure (e.g., in the range of pH 4.0 to pH 6.0; or above pH 4.0, above pH 4.1, above pH 4.2, above pH 4.3, above pH 4.4, above pH 4.5, above pH 4.6, above pH 4.7, above pH 4.8, above pH 4.9, above pH 5.0, above pH 5.1, above pH 5.2, above pH 5.3, above pH 5.4, above pH 5.5, above pH 5.6, above pH 5.7, above pH 5.8, above pH 5.9, above pH 6.0, above pH 6.1, above pH 6.2, above pH 6.3, above pH 6.4, or above pH 6.5, with the maximum elution being pH 6.0, pH 6.1, pH 6.2, pH 6.3, pH 6.4, or pH 6.5).

In some other embodiment, a step-wise elution can be used. For example, a first buffer is used to wash the chromatography matrix, and a second buffer is used to elute immunoglobulins. The second buffer can have an appropriate pH as described in this disclosure (e.g., pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0). In some cases, a third buffer can be used to determine the total amount of antibodies that can be eluted from chromatography, which can be used for verification of total elution or yield. The pH for the third buffer should be lower than the pH of the second buffer (e.g., pH 2.0, pH 2.1, pH 2.2, pH 2.3, pH 2.4, pH 2.5, pH 2.6, pH 2.7, pH 2.8, pH 2.9, pH 3.0, or lower than pH 2.0).

The disclosure also provides methods of purifying immunoglobulins. The methods include the steps of contacting the chromatography ligands described herein with a solution comprising immunoglobulins; washing the chromatography ligand with a first buffer; and eluting the immunoglobulins with a second buffer having a selected pH. The selected pH can be any pH as described in this disclosure. In some embodiments, the selected pH is greater than 4.0 (e.g., pH 4.5, pH 4.7).

The disclosure also provides methods of purifying immunoglobulins. The methods include the steps of contacting the chromatography ligands described herein with a solution comprising immunoglobulins; washing the chromatography ligands with a buffer, wherein the buffer has a linear pH gradient over time; and collecting immunoglobulins in a selected pH. The linear pH gradient can be from about pH 8.0 to about pH 3.0. In some embodiments, the selected pH is from about 6.0 to about 4.0 (e.g., from about 6.0 to about 4.5, or from about 6.0 to about 4.7).

In some embodiments, the recovery yield at various described conditions can be greater than 50%, 60%, 70%, 80%, 90%, 95%, 96%, 97%, 98%, or 99%.

EXAMPLES

The invention is further described in the following examples, which do not limit the scope of the invention described in the claims.

Example 1: Protein Design and Engineering

Exemplary ligands based on Formula I described above were designed. Briefly, a TetraZ-H (i.e. ZHZHZHZH) and a PentaZ-H (i.e. ZHZHZHZHZH), wherein Z represented SPA domain Z, and H represented a helical domain (as the spacer domain), were designed as the new affinity ligands for IgG binding and elution tests. The diagram representation of TetraZ-H and PentaZ-H was shown in FIG. 2.

Figure 4:
FIG. 4 is a diagram showing the central helical region of the connecting helix of ribosomal protein L9 from *Bacillus stearothermophilus*. This helical region can be used as a spacer domain, and the sequence is shown below the diagram (SEQ ID NO: 8).

The helical domain H was chosen from the central segment of the connecting helix in ribosomal protein L9 from *B. stearothermophilus*. The L9 connecting helix, which was conserved in a number of organisms, was shown to be exceptionally stable. As shown in FIG. 4, the central segment of the connecting helix has about 18 residues (forming about 4 helical turns and having roughly same length as Z domain) and is primarily hydrophilic. Thus, this helix (i.e. domain H) is suitable to serve the purpose as a spacer domain in TetraZ-H and PentaZ-H.

Three additional ligands, which did not contain any spacer domains, were designed as controls. The three control ligands are TetraZ (ZZZZ), PentaZ (ZZZZZ) and PentaZ$_{D36H}$ ($Z_{D36H} Z_{D36H} Z_{D36H} Z_{D36H} Z_{D36H}$), respectively. The linkage of the tandem repeats of the IgG binding domains in these designed ligands is exactly the same as that of the native SPA or commercially available SPA variants, for example, MabSelect SuRe of GE Healthcare. Their diagram representation is shown in FIG. 3. The domain $Z_{D36H}$ is a variant of domain Z with a single mutation of Asp36His. The mutagen, $Z_{D36H}$, according to U.S. Pat. No. 9,382,297 B2, showed higher elution pH than the Z domain.

All the designed ligands mentioned above were also designed to have a C-terminal poly-His-tag to facilitate purification and a Cysteine tag to facilitate matrix coupling. The sequence for each ligand is listed in Table 1.

TABLE 1

| Name of Ligand | Sequence ID | Number of Z domain | Number of H domain |
| --- | --- | --- | --- |
| PentaZ | SEQ ID NO: 9 | 5 | 0 |
| PentaZ-H | SEQ ID NO: 10 | 5 | 5 |
| TetraZ | SEQ ID NO: 12 | 4 | 0 |
| TetraZ-H | SEQ ID NO: 13 | 4 | 4 |
| PentaZ$_{D36H}$ | SEQ ID NO: 11 | 5 | 0 |

Example 2: Gene Synthesis, Protein Expression and Purification of SPA Ligands

Synthetic genes encoding the proteins listed in Table 1 were obtained from commercial gene synthesis companies. All the synthesized genes were codon optimized for *Pichia* expression system and were subcloned into *Pichia* expression vectors obtained from BioGrammatics (Carlsbad, Calif.). All the sequences were verified to be correct before yeast transformation. The transformation and selection of *Pichia* strains were done according to the standard protocols recommended by BioGrammatics (Carlsbad, Calif.). The *Pichia* cell culture and protein expression were described, e.g., in Maria Weidner, et. al. Expression of Recombinant Proteins in the Methylotrophic Yeast *Pichia pastoris*. J Vis Exp. 2010; (36): 1862; and Thermo Fisher Scientific, *Pichia* Fermentation Process Guidelines; each of which is incorporated by reference in its entirety.

TABLE 2

| Name of Gene | Expression system | Expression Vectors | Expression Method |
| --- | --- | --- | --- |
| TetraZ-H | *Pichia pastoris* | pJAGalpha | Secretion |
| PentaZ-H | *Pichia pastoris* | pJAGalpha | Secretion |
| TetraZ | *Pichia pastoris* | pJAGalpha | Secretion |
| PentaZ | *Pichia pastoris* | pJAGalpha | Secretion |
| PentaZ$_{D36H}$ | *Pichia pastoris* | pJAGalpha | Secretion |

The expressed proteins were secreted into *Pichia* culture media. The culture media were harvested and clarified for downstream purification. The purification of the expressed proteins was done by two steps. In the first step, the target protein was captured by passing the clarified media through a column containing Ni-NTA resin. The bound protein, which harbors a poly-His tag, was eluted with a gradient of Imidazole solution. The elution fraction that contains the target protein was buffer-exchanged for the second step of cationic exchange chromatography. The pH of the protein solution was checked and adjusted to pH 4.5 and the conductivity was maintained at 10 ms/cm. The solution was then passed through a SP column and the bound protein was eluted with a gradient solution of salts. Finally, the purified protein was dialyzed against a buffer free of free amines (e.g. 1 × PBS). And the protein concentration was adjusted to about 10 mg/ml.

Example 3: SPA Affinity Resin and Column Preparation

Crosslinked 4% agarose beads with diameter of 45-165 μm were used for SPA ligand immobilization. The bead matrix was first washed and re-suspended in 0.5 M NaOH. 1,4-Butanediol diglycidyl ether (BDE) was added to the solution to the final concentration of 30% vol/vol. The mixture solution was stirred vigorously at 22-24° C. for 16-18 hours. Then the activated beads were washed extensively with water and ethanol until the free BDE was removed. The beads were activated with epoxy groups and stored in water at 4° C. before ligand coupling.

The epoxy activated agarose beads were sucked dry in a fritted funnel and 1 ml of beads was used for a ligand coupling experiment. First, a couple buffer was made as the following. In a 50 ml conical tube, 0.21 g of Sodium Bicarbonate, 3.6 g of Sodium Sulfate, 0.3 g of EDTA, and 20 ml of water were added and mixed. The pH of the coupling buffer in the conical tube was checked and adjusted to pH 7.5. About 5 ml of the ligand protein solution (with concentration of about 10 mg/ml) was added to the conical tube. The final total protein was about 50 mg, which exceeded the maximum amount of protein that could be coupled to the beads. The five protein ligands, TetraZ-H, PentaZ-H, TetraZ, PentaZ and PentaZ$_{D36H}$ were treated equally. Finally, the activated agarose beads (1 ml) were added to the solution. The mixture was gently shaken overnight (e.g. 16-18 h) at room temperature (i.e. 22-25° C.). After ligand immobilization, the agarose beads were washed with extensively with water and a Tris-NaCl buffer (Tris 100 mM, pH 9.0, NaCl 150 mM). To deactivate any un-reacted epoxy groups, 1 M ethanolamine was added to the beads solution for 4 hours at room temperature.

The five SPA ligand coupled resins, TetraZ-H, PentaZ-H, TetraZ and PentaZ, PentaZ$_{D36H}$ were finally packed into 1 ml column cartridges, respectively. The 1 ml column cartridge used in the experiments has inter diameter of 0.72 cm and inter length of 2.50 cm, similar to GE's 1 ml Hitrap HP column.

Example 4: Human IgG Binding and Elution Tests for TetraZ-H and TetraZ

Materials and Methods

Purified human poly clonal IgG from Biocell Laboratories, Inc. was used for the binding tests. The IgG was dissolved in 1×PBS and filtered with 0.2 μm membrane. The concentration of the IgG was adjusted to 10 mg/ml.

Buffers for IgG binding test were prepared as the following.

Buffer A: 75 mM Tris, pH 8.0, 150 mM NaCl, EDTA 1 mM.

Buffer B: 0.1 M Citric Acid, pH 2.8.

One-ml columns of TetraZ-H and TetraZ protein A resin were prepared and equilibrated with Buffer A, respectively. GE AKTA Explorer 100 was used for running the columns. Total 2.0 ml of the IgG solution was injected to each column at flow rate of 0.5 ml/min (i.e. 2 min residence time). Each column was washed with 12 ml of Buffer A at flow rate of 3 mg/min after sample injection. Then the bound IgG was eluted with a pH gradient by running Buffer B from 0-100% for 15 min at flow rate of 3 ml/min. The chromatograms of each column running were recorded.

Results

Figure 5:
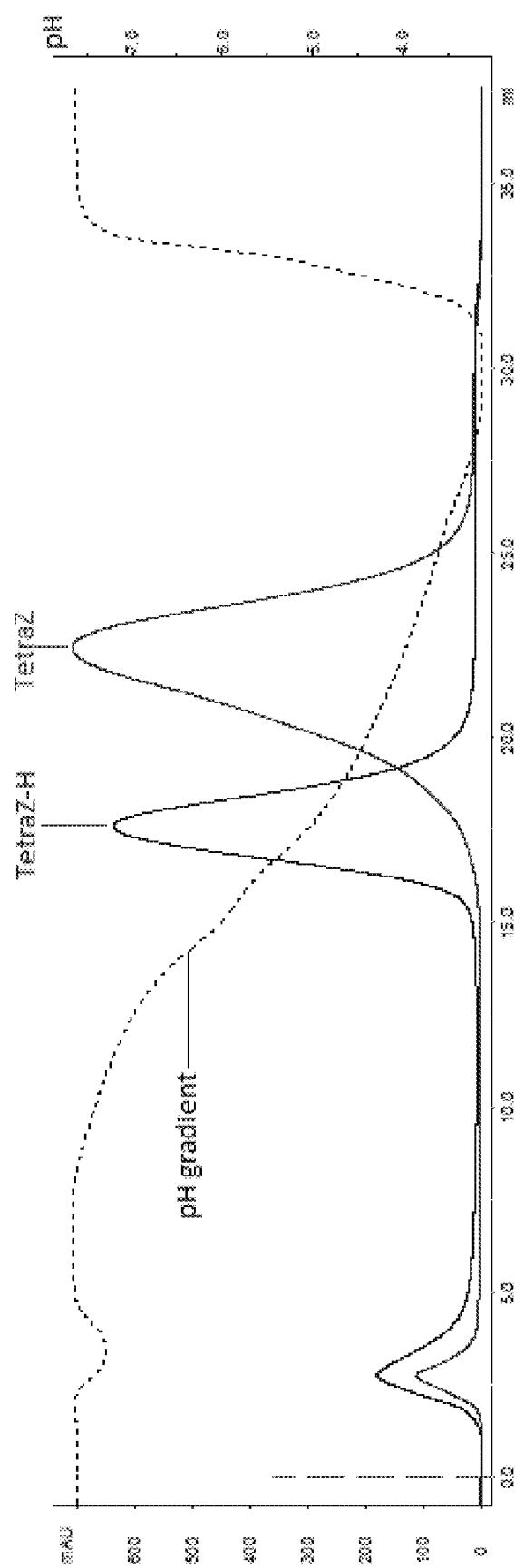
FIG. 5 is a graph showing pH gradient elution profile for TetraZ-H and TetraZ agarose resins packed in 1-ml column. The pH value corresponding to the center of elution peaks for TetraZ-H and TetraZ are 5.02 and 3.91, respectively.

The eluent pH dropped in a roughly linear model when Buffer B was running from 0-100%. The overlaid elution curves for the three different columns were shown in FIG. 5. The pH value at the peak of each eluent was measured and listed on Table 3.

TABLE 3

|  | TetraZ-H | TetraZ |
| --- | --- | --- |
| Peak Elution pH | 5.02 | 3.91 |

TetraZ-H had significantly higher elution pH than that of TetraZ. Since TetraZ-H and TetraZ share the same IgG binding domains, the differential elution pH seen in the two ligands can be attributed to the presence of the spacer helix domains in TetraZ-H. Based on FIG. 5, the elution peak of TetraZ-H is also narrower than that of TetraZ, indicating the helix H domains can improve the elution profile in addition to the elution pH.

Example 5: Human IgG Binding and Elution for PentaZ-H, PentaZ, and PentaZ$_{D36H}$ Materials and Methods Purified human poly clonal IgG from Biocell Laboratories (Compton, Calif.) was used for the binding tests. The IgG was dissolved in 1×PBS and filtered with 0.2 μm in membrane. The concentration of the IgG was adjusted to 10 mg/ml.

Buffers for IgG binding test were prepared as the following.

Buffer A: 75 mM Tris, pH 8.0, 150 mM NaCl, EDTA 1 mM.

Buffer B: 0.1 M Citric Acid, pH 2.8.

One-ml columns of PentaZ-H, PentaZ and HiTrap Protein A HP (from GE), respectively, were prepared and equilibrated with Buffer A. GE AKTA Explorer 100 was used for running the columns. Total 2.0 ml of the IgG solution was injected to each column at flow rate of 0.5 ml/min (i.e. 2 min residence time). The column was washed with 12 ml of Buffer A at flow rate of 3 mg/min at flow rate of 2 mg/min after sample injection. Then the bound IgG was eluted with a pH gradient by running Buffer B from 0-100% for 15 min at flow rate of 3 ml/min.

Results

The eluent pH dropped in a roughly linear model when Buffer B was running from 0-100%. The overlaid elution curves for the three different columns were shown in FIG. 6. The pH value at the peak of each eluent was measured and listed on Table 4.

TABLE 4

|  | PentaZ-H | PentaZ | PentaZ$_{D36H}$ |
| --- | --- | --- | --- |
| Peak Elution pH | 4.91 | 3.86 | 4.28 |

PentaZ-H had significantly higher elution pH than both PentaZ and PentaZ$_{D36H}$. In contrast, PentaZ, containing the same IgG binding domains as PentaZ-H, had much lower elution pH. Interestingly, the Asp36 to His mutation did increase the elution pH for about 0.3 units. However, the elution peak of PentaZ$_{D36H}$ seems broader than that of PentaZ-H, suggesting PentaZ$_{D36H}$'s residual non-specific binding, which is also seen in PentaZ.

Example 6: Step-wise Elution of PentaZ-H and HiTrap Protein A HP

Materials and Methods

Purified human poly clonal IgG from Biocell Laboratories (Compton, Calif.) was used for the binding tests. The IgG was dissolved in 1×PBS and filtered with 0.2 μm membrane. The concentration of the IgG was adjusted to 10 mg/ml.

Buffers for IgG binding test were prepared as the following.

Buffer A: 1 × PBS, pH 7.6 (137 mM NaCl; 2.7 mM KCl; 4.3 mM Na2HPO4; 1.47 mM KH2PO4).

Buffer B1: 0.1 M Citric Acid, pH 4.7.

Buffer B2: 0.1 M Citric Acid, pH 4.3. Buffer B3: 0.1 M Citric Acid, pH 4.0.

Buffer B4: 0.1 M Citric Acid, pH 4.7.

One-ml columns of PentaZ-H and HiTrap Protein A HP (from GE Healthcare) were prepared and equilibrated with Buffer A respectively. GE AKTA Explorer 100 was used for running the columns. Total 3.5 ml of the IgG solution was injected to each column at flow rate of 0.5 ml/min (i.e. 2 min residence time). The column was washed with 12 ml of Buffer A1 at flow rate of 2 mg/min after sample injection. Then the bound IgG was eluted at pH 4.75 with buffer B1 for 12 ml, at pH 4.25 with buffer B2 for 12 ml, at pH 4.0 with buffer B3 for 12 ml and finally at pH 2.8 with buffer B4 for 12 ml. Each eluent buffer was saved and measured for protein concentration.

Results

Figure 8:
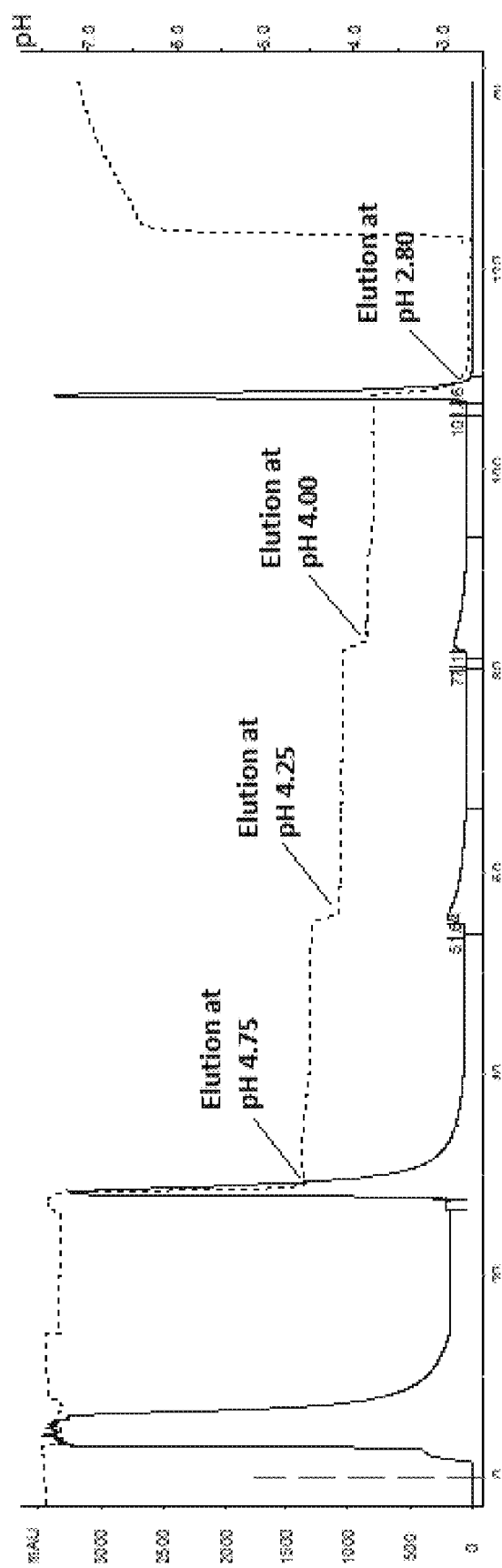
FIG. 8 is a graph showing pH step-wise elution profile of a GE Hitrap Protein A HP column.

The step-wise elution chromatograms for PentaZ-H and Hitrap Protein A HP were shown in FIG. 7 and FIG. 8, respectively. In FIG. 8, about 53% of the antibody was first eluted at pH 4.75, and the remaining antibodies were not eluted to until the elution pH reaches 2.8. In contrast, in FIG. 7, about 99% of antibodies were eluted at pH 4.75.

Table 5 lists the yield and percentage of the elution at each elution pH. For PentaZ-H, over 97-99% of bound IgG was eluted at pH 4.75, less than 1% at pH 4.25 and close to zero at pH 2.8. For HiTrap Protein A HP, about 53% was eluted at pH 4.75, about 3% at pH 4.25, about 2% at pH 4.0, and over 40% at pH 2.8.

TABLE 5

|  | Normalized yield at different pH | | | |
| --- | --- | --- | --- | --- |
|  | pH 4.75 | pH 4.25 | pH 4.0 | pH 2.80 |
| PentaZ-H | 99% | 1% | N/A | 0 |
| HiTrap Protein A HP | 53% | 3% | 2% | 42% |

The recovery rate for PentaZ-H at mild condition, for example, at pH 4.5 or above, is close to 100%. In contrast, the SPA ligand without the spacer domain such as the native SPA requires strong acidic condition for elution, which may cause significant amount of antibody aggregation.

Example 7: Elution pH of PentaZ-H and PentaZ for a Monoclonal Antibody

Materials and Methods

Total 1 mg of a commercial monoclonal antibody, which belongs to mouse IgG2 class, was used for plate-based binding assay. The monoclonal antibody was diluted with 1 × PBS (pH 7.2) to 100 μg/ml before binding. PentaZ-H and PentaZ protein were immobilized on a Pierce™ Maleimide Activated Plate through their C-terminal Cys residues. Both PentaZ-H and PentaZ were diluted to 100 μg/ml in 1 × PBS before immobilization. The procedure of immobilization was done based on the manufacturer's protocol. After 5 hours of immobilization, the plate was washed with 1×PBS (pH 7.2) and blocked with a blocking buffer for overnight. The plate was equilibrated with 1 × PBS (pH 7.2) before binding test.

For binding test, 100 μl of the antibody solution was added to each well that was covalently coated with PentaZ-H. After 10 min of incubation at room temperature with gentle shaking, the plate was washed with 300 ul of 1×PBS (pH 7.2) for 6 times. All the solution was completely aspirated before elution.

Four different pH of elution buffer (pH 4.7, pH 4.3, pH 4.0 and pH 2.8 of 0.1 M Citrate) were made for step-wise elution. From high pH to low pH, 50 μl of each elution buffer was added to each well, incubated for 5 min at room temperature and collected. For each elution pH, three duplicates were done. As a control, a single step elution was also made with the buffer of pH 2.8. After elution, the protein concentration of the eluted IgG was measured with Pierce BCA Protein Assay Kit. The values were averaged for all duplicates.

Results

Table 6 shows binding and elution results of PentaZ-H for the monoclonal antibody. IgG was only detected in the pH 4.7 elution, but not in pH 4.3, pH 4.0 or pH 2.8. The amount of eluted IgG at pH 4.7 is very close to that of the single step elution at pH 2.8. For the control group of PentaZ, about 50.5% of IgG was eluted at pH 4.7, 6% at pH 4.3, 16% at pH 4.0 and 27.5% at pH 2.8.

TABLE 6

|  | Step-wise Elution | | | | Single-step elution |
|---|---|---|---|---|---|
|  | pH 4.7 | pH 4.3 | pH 4.0 | pH 2.8 | pH 2.8 |
| Total Elution PentaZ-H (μg) | 228.6 | Non-detectable | Non-detectable | Non-detectable | 235.2 |
| PentaZ-H Recoveiy rate | 100% | N/A | N/A | N/A | 100% |

TABLE 6-continued

|  | Step-wise Elution | | | | Single-step elution |
|---|---|---|---|---|---|
|  | pH 4.7 | pH 4.3 | pH 4.0 | pH 2.8 | pH 2.8 |
| Total Elution PentaZ (μg) | 93.5 | 11.1 | 29.6 | 50.8 | 189.7 |
| PentaZ Recovery rate | 50.5% | 6.0% | 16.0% | 27.5% | 100% |

This is a plate-based binding and elution experiment, which is an alternative of column based chromatographic experiment described above. The PentaZ-H ligand, when immobilized on a plate, allows the complete elution of bound IgG molecules at pH 4.7. As a control, PentaZ, which is in the classic format of SPA, had large amount of bound IgG before encountering the buffers with pH lower than 4.0.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising at least two binding units and at least one spacer domain, wherein every two neighboring binding units are separated by at least one spacer domain, and each binding unit comprises one or two immunoglobulin binding domains, wherein the spacer domain comprises an alpha helix.

2. The polypeptide of claim 1, wherein the spacer domain is not a random coil or a disordered loop at pH about 4.5 to about 7.

3. The polypeptide of claim 1, wherein every two neighboring binding units are separated by one spacer domain.

4. The polypeptide of claim 1, wherein the immunoglobulin binding domain is a *Staphylococcal* Protein A (SPA) immunoglobulin binding domain.

5. The polypeptide of claim 1, wherein the immunoglobulin binding domain is domain A of SPA, domain B of SPA, domain C of SPA, domain D of SPA, or domain E of SPA.

6. The polypeptide of claim 1, wherein the immunoglobulin binding domain is domain Z.

7. The polypeptide of claim 1, wherein the immunoglobulin binding domain is domain $Z_{D36H}$.

8. The polypeptide of claim 1, wherein the immunoglobulin binding domain is a *Streptococcal* Protein G (SPG) immunoglobulin binding domain.

9. The polypeptide of claim 1, wherein at least one immunoglobulin binding domain is a SPA immunoglobulin binding domain, and at least one immunoglobulin binding domain is a SPG immunoglobulin binding domain.

10. The polypeptide of claim 1, wherein the spacer domain is a domain of glucagon (SEQ ID NO: 14), a connecting helix of calmodulin (SEQ ID NO: 15), a single alpha-helix domain (SAH) of Myosin-10 (SEQ ID NO: 16), a Sumo domain (SEQ ID NO: 17), an EGF domain (SEQ ID NO: 18), or an ubiquitin-associated (UBA) domain of Rad23A (SEQ ID NO: 19).

11. The polypeptide of claim 1, wherein the polypeptide comprises a sequence as defined by Formula II:

$$S_{0-1}(R_{1-2}S)_n R_{0-2} \quad \text{(Formula II)}$$

wherein

R represents an immunoglobulin binding domain;

S represents a spacer domain;

n is an integer, indicating the number of repeating units in the protein, and n can be equal to 1 or larger than 1.

12. The polypeptide of claim 11, wherein the polypeptide comprises a sequence as defined by Formula III:

$$RSRSRSRS \quad \text{(Formula III)}.$$

13. The polypeptide of claim 11, wherein the polypeptide comprises a sequence as defined by Formula IV:

$$RR-S-RR-S-RR-S \quad \text{(Formula IV)}.$$

14. A vector comprising a polynucleotide encoding the polypeptide of claim 1.

15. A chromatography ligand comprising the polypeptide of claim 1.

16. The chromatography ligand of claim 15, wherein the chromatography ligand has a recovery yield over 60% with elution pH at 4.7 or higher.

17. The chromatography ligand of claim 15, wherein the chromatography ligand is immobilized on a matrix.

18. A method of purifying immunoglobulins, the method comprising contacting the chromatography ligand of claim 15 with a solution comprising immunoglobulins;

washing the chromatography ligand with a first buffer; and eluting the immunoglobulins with a second buffer having a selected pH, wherein the selected pH is greater than 4.0.

19. A method of purifying immunoglobulins, the method comprising contacting the chromatography ligand of claim 15 with a solution comprising immunoglobulins;

washing the chromatography ligand with a buffer, wherein the buffer has a linear pH gradient;

and collecting immunoglobulins at a selected pH.

* * * * *

SEQUENCE LISTING

<160> NUMBER OF SEQ ID NOS: 22

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus

<400> SEQUENCE: 2

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 3
<211> LENGTH: 58
<212> TYPE: PRT
<213> ORGANISM: Staphylococcus aureus

<400> SEQUENCE: 3

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

<210> SEQ ID NO 4
<211> LENGTH: 60
<212> TYPE: PRT
<213> ORGANISM: Staphylococcus aureus

<400> SEQUENCE: 4

```
Ala Ala Asn Ala Ala Gln His Asp Glu Ala Gln Gln Asn Ala Phe Tyr
1               5                   10                  15

Gln Val Leu Asn Met Pro Asn Leu Ala Asp Gln Arg Asn Gly Phe
            20                  25                  30

Ile Gln Ser Leu Lys Asp Asp Pro Ser Gln Ser Ala Asn Val Leu Gly
        35                  40                  45

Glu Ala Gln Lys Leu Asn Asp Ser Gln Ala Pro Lys
    50                  55                  60
```

<210> SEQ ID NO 5
<211> LENGTH: 61
<212> TYPE: PRT
<213> ORGANISM: Staphylococcus aureus

<400> SEQUENCE: 5

```
Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic

```
<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 18
<212> TYPE: PRT
<213> ORGANISM: Bacillus stearothermophilus

<400> SEQUENCE: 8

Glu Ala Gln Lys Gln Lys Glu Gln Arg Gln Ala Ala Glu Glu Leu Ala
1               5                   10                  15

Asn Ala

<210> SEQ ID NO 9
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
    50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
```

```
                    85                  90                  95
Ser Gln Ser Ala Asn Leu Leu Ala Glu Ala Lys Lys Leu Asn Asp Ala
                100                 105                 110
Gln Ala Pro Lys Val Asp Asn Lys Phe Asn Lys Glu Gln Gln Asn Ala
                115                 120                 125
Phe Tyr Glu Ile Leu His Leu Pro Asn Leu Asn Glu Glu Gln Arg Asn
            130                 135                 140
Ala Phe Ile Gln Ser Leu Lys Asp Asp Pro Ser Gln Ser Ala Asn Leu
145                 150                 155                 160
Leu Ala Glu Ala Lys Lys Leu Asn Asp Ala Gln Ala Pro Lys Val Asp
                165                 170                 175
Asn Lys Phe Asn Lys Glu Gln Gln Asn Ala Phe Tyr Glu Ile Leu His
                180                 185                 190
Leu Pro Asn Leu Asn Glu Glu Gln Arg Asn Ala Phe Ile Gln Ser Leu
                195                 200                 205
Lys Asp Asp Pro Ser Gln Ser Ala Asn Leu Leu Ala Glu Ala Lys Lys
210                 215                 220
Leu Asn Asp Ala Gln Ala Pro Lys Val Asp Asn Lys Phe Asn Lys Glu
225                 230                 235                 240
Gln Gln Asn Ala Phe Tyr Glu Ile Leu His Leu Pro Asn Leu Asn Glu
                245                 250                 255
Glu Gln Arg Asn Ala Phe Ile Gln Ser Leu Lys Asp Asp Pro Ser Gln
                260                 265                 270
Ser Ala Asn Leu Leu Ala Glu Ala Lys Lys Leu Asn Asp Ala Gln Ala
                275                 280                 285
Pro Lys His His His His His His Cys Cys Lys Cys
                290                 295                 300

<210> SEQ ID NO 10
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Asp Asn Lys Phe Asn Lys Glu Gln Gln Asn Ala Phe Tyr Glu Ile
1               5                   10                  15
Leu His Leu Pro Asn Leu Asn Glu Glu Gln Arg Asn Ala Phe Ile Gln
                20                  25                  30
Ser Leu Lys Asp Asp Pro Ser Gln Ser Ala Asn Leu Leu Ala Glu Ala
                35                  40                  45
Lys Lys Leu Asn Asp Ala Gln Ala Pro Lys Glu Ala Gln Lys Gln Lys
            50                  55                  60
Glu Gln Arg Gln Ala Ala Glu Glu Leu Ala Asn Ala Val Asp Asn Lys
65                  70                  75                  80
Phe Asn Lys Glu Gln Gln Asn Ala Phe Tyr Glu Ile Leu His Leu Pro
                85                  90                  95
Asn Leu Asn Glu Glu Gln Arg Asn Ala Phe Ile Gln Ser Leu Lys Asp
                100                 105                 110
Asp Pro Ser Gln Ser Ala Asn Leu Leu Ala Glu Ala Lys Lys Leu Asn
            115                 120                 125
Asp Ala Gln Ala Pro Lys Glu Ala Gln Lys Gln Lys Glu Gln Arg Gln
            130                 135                 140
```

```
Ala Ala Glu Glu Leu Ala Asn Ala Val Asp Asn Lys Phe Asn Lys Glu
145                 150                 155                 160

Gln Gln Asn Ala Phe Tyr Glu Ile Leu His Leu Pro Asn Leu Asn Glu
            165                 170                 175

Glu Gln Arg Asn Ala Phe Ile Gln Ser Leu Lys Asp Asp Pro Ser Gln
        180                 185                 190

Ser Ala Asn Leu Leu Ala Glu Ala Lys Lys Leu Asn Asp Ala Gln Ala
    195                 200                 205

Pro Lys Glu Ala Gln Lys Gln Lys Glu Gln Arg Gln Ala Ala Glu Glu
210                 215                 220

Leu Ala Asn Ala Val Asp Asn Lys Phe Asn Lys Glu Gln Gln Asn Ala
225                 230                 235                 240

Phe Tyr Glu Ile Leu His Leu Pro Asn Leu Asn Glu Glu Gln Arg Asn
            245                 250                 255

Ala Phe Ile Gln Ser Leu Lys Asp Asp Pro Ser Gln Ser Ala Asn Leu
        260                 265                 270

Leu Ala Glu Ala Lys Lys Leu Asn Asp Ala Gln Ala Pro Lys Glu Ala
    275                 280                 285

Gln Lys Gln Lys Glu Gln Arg Gln Ala Ala Glu Glu Leu Ala Asn Ala
290                 295                 300

Val Asp Asn Lys Phe Asn Lys Glu Gln Gln Asn Ala Phe Tyr Glu Ile
305                 310                 315                 320

Leu His Leu Pro Asn Leu Asn Glu Glu Gln Arg Asn Ala Phe Ile Gln
            325                 330                 335

Ser Leu Lys Asp Asp Pro Ser Gln Ser Ala Asn Leu Leu Ala Glu Ala
        340                 345                 350

Lys Lys Leu Asn Asp Ala Gln Ala Pro Lys Glu Ala Gln Lys Gln Lys
    355                 360                 365

Glu Gln Arg Gln Ala Ala Glu Glu Leu Ala Asn Ala His His His His
370                 375                 380

His His His Cys Cys Lys Cys
385                 390

<210> SEQ ID NO 11
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
    50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys His Asp Pro
            85                  90                  95

Ser Gln Ser Ala Asn Leu Leu Ala Glu Ala Lys Lys Leu Asn Asp Ala
        100                 105                 110
```

```
Gln Ala Pro Lys Val Asp Asn Lys Phe Asn Lys Glu Gln Gln Asn Ala
        115                 120                 125

Phe Tyr Glu Ile Leu His Leu Pro Asn Leu Asn Glu Gln Arg Asn
    130                 135                 140

Ala Phe Ile Gln Ser Leu Lys His Asp Pro Ser Gln Ser Ala Asn Leu
145                 150                 155                 160

Leu Ala Glu Ala Lys Lys Leu Asn Asp Ala Gln Ala Pro Lys Val Asp
                165                 170                 175

Asn Lys Phe Asn Lys Glu Gln Gln Asn Ala Phe Tyr Glu Ile Leu His
                180                 185                 190

Leu Pro Asn Leu Asn Glu Glu Gln Arg Asn Ala Phe Ile Gln Ser Leu
        195                 200                 205

Lys His Asp Pro Ser Gln Ser Ala Asn Leu Leu Ala Glu Ala Lys Lys
    210                 215                 220

Leu Asn Asp Ala Gln Ala Pro Lys Val Asp Asn Lys Phe Asn Lys Glu
225                 230                 235                 240

Gln Gln Asn Ala Phe Tyr Glu Ile Leu His Leu Pro Asn Leu Asn Glu
                245                 250                 255

Glu Gln Arg Asn Ala Phe Ile Gln Ser Leu Lys His Asp Pro Ser Gln
            260                 265                 270

Ser Ala Asn Leu Leu Ala Glu Ala Lys Lys Leu Asn Asp Ala Gln Ala
        275                 280                 285

Pro Lys His His His His His His Cys Cys Lys Cys
        290                 295                 300

<210> SEQ ID NO 12
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys Val Asp Asn Lys Phe Asn Lys Glu Gln Gln Asn Ala
        115                 120                 125

Phe Tyr Glu Ile Leu His Leu Pro Asn Leu Asn Glu Gln Arg Asn
    130                 135                 140

Ala Phe Ile Gln Ser Leu Lys Asp Asp Pro Ser Gln Ser Ala Asn Leu
145                 150                 155                 160

Leu Ala Glu Ala Lys Lys Leu Asn Asp Ala Gln Ala Pro Lys Val Asp
```

```
                    165                 170                 175

Asn Lys Phe Asn Lys Glu Gln Gln Asn Ala Phe Tyr Glu Ile Leu His
                180                 185                 190

Leu Pro Asn Leu Asn Glu Glu Gln Arg Asn Ala Phe Ile Gln Ser Leu
            195                 200                 205

Lys Asp Asp Pro Ser Gln Ser Ala Asn Leu Leu Ala Glu Ala Lys Lys
        210                 215                 220

Leu Asn Asp Ala Gln Ala Pro Lys His His His His His His Cys
225                 230                 235                 240

Cys Lys Cys

<210> SEQ ID NO 13
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Glu Ala Gln Lys Gln Lys
    50                  55                  60

Glu Gln Arg Gln Ala Ala Glu Glu Leu Ala Asn Ala Val Asp Asn Lys
65                  70                  75                  80

Phe Asn Lys Glu Gln Gln Asn Ala Phe Tyr Glu Ile Leu His Leu Pro
                85                  90                  95

Asn Leu Asn Glu Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125

Asp Ala Gln Ala Pro Lys Glu Ala Gln Lys Gln Lys Glu Gln Arg Gln
    130                 135                 140

Ala Ala Glu Glu Leu Ala Asn Ala Val Asp Asn Lys Phe Asn Lys Glu
145                 150                 155                 160

Gln Gln Asn Ala Phe Tyr Glu Ile Leu His Leu Pro Asn Leu Asn Glu
                165                 170                 175

Glu Gln Arg Asn Ala Phe Ile Gln Ser Leu Lys Asp Asp Pro Ser Gln
            180                 185                 190

Ser Ala Asn Leu Leu Ala Glu Ala Lys Lys Leu Asn Asp Ala Gln Ala
        195                 200                 205

Pro Lys Glu Ala Gln Lys Gln Lys Glu Gln Arg Gln Ala Ala Glu Glu
    210                 215                 220

Leu Ala Asn Ala Val Asp Asn Lys Phe Asn Lys Glu Gln Gln Asn Ala
225                 230                 235                 240

Phe Tyr Glu Ile Leu His Leu Pro Asn Leu Asn Glu Glu Gln Arg Asn
                245                 250                 255

Ala Phe Ile Gln Ser Leu Lys Asp Asp Pro Ser Gln Ser Ala Asn Leu
            260                 265                 270

Leu Ala Glu Ala Lys Lys Leu Asn Asp Ala Gln Ala Pro Lys His His
```

```
                 275                 280                 285

His His His His His Cys Cys Lys Cys
    290                 295

<210> SEQ ID NO 14
<211> LENGTH: 20
<212> TYPE: PRT
<213> ORGANISM: Homo sapiens

<400> SEQUENCE: 14

Thr Ser Asp Tyr Ser Lys Tyr Leu Asp Ser Arg Arg Ala Gln Asp Phe
1               5                   10                  15

Val Gln Trp Leu
            20

<210> SEQ ID NO 15
<211> LENGTH: 23
<212> TYPE: PRT
<213> ORGANISM: Paramecium tetraurelia

<400> SEQUENCE: 15

Phe Leu Ser Leu Met Ala Arg Lys Met Lys Glu Gln Asp Ser Glu Glu
1               5                   10                  15

Glu Leu Ile Glu Ala Phe Lys
            20

<210> SEQ ID NO 16
<211> LENGTH: 27
<212> TYPE: PRT
<213> ORGANISM: Homo sapiens

<400> SEQUENCE: 16

Glu Ile Asp Ser Thr Trp Ser Ala Leu Glu Lys Ala Glu Gln Glu His
1               5                   10                  15

Ala Glu Ala Leu Arg Ile Glu Leu Lys Arg Gln
            20                  25

<210> SEQ ID NO 17
<211> LENGTH: 75
<212> TYPE: PRT
<213> ORGANISM: Homo sapiens

<400> SEQUENCE: 17

Glu Gly Glu Tyr Ile Lys Leu Lys Val Ile Gly Gln Asp Ser Ser Glu
1               5                   10                  15

Ile His Phe Lys Val Lys Met Thr Thr His Leu Lys Lys Leu Lys Glu
            20                  25                  30

Ser Tyr Cys Gln Arg Gln Gly Val Pro Met Asn Ser Leu Arg Phe Leu
        35                  40                  45

Phe Glu Gly Gln Arg Ile Ala Asp Asn His Thr Pro Lys Glu Leu Gly
    50                  55                  60

Met Glu Glu Glu Asp Val Ile Glu Val Tyr Gln
65                  70                  75

<210> SEQ ID NO 18
<211> LENGTH: 48
<212> TYPE: PRT
<213> ORGANISM: Homo sapiens

<400> SEQUENCE: 18

Asn Ser Tyr Pro Gly Cys Pro Ser Ser Tyr Asp Gly Tyr Cys Leu Asn
```

```
                1               5                   10                  15
Gly Gly Val Cys Met His Ile Glu Ser Leu Asp Ser Tyr Thr Cys Asn
                    20                  25                  30
Cys Val Ile Gly Tyr Ser Gly Asp Arg Cys Gln Thr Arg Asp Leu Arg
            35                  40                  45
```

<210> SEQ ID NO 19
<211> LENGTH: 40
<212> TYPE: PRT
<213> ORGANISM: Homo sapiens

<400> SEQUENCE: 19

```
Ser Glu Tyr Glu Thr Met Leu Thr Glu Ile Met Ser Met Gly Tyr Glu
1               5                   10                  15
Arg Glu Arg Val Val Ala Ala Leu Arg Ala Ser Tyr Asn Asn Pro His
                20                  25                  30
Arg Ala Val Glu Tyr Leu Leu Thr
            35                  40
```

<210> SEQ ID NO 20
<211> LENGTH: 70
<212> TYPE: PRT
<213> ORGANISM: Streptococcus dysgalactiae

<400> SEQUENCE: 20

```
Thr Tyr Lys Leu Ile Leu Asn Gly Lys Thr Leu Lys Gly Glu Thr Thr
1               5                   10                  15
Thr Glu Ala Val Asp Ala Ala Thr Ala Glu Lys Val Phe Lys Gln Tyr
                20                  25                  30
Ala Asn Asp Asn Gly Val Asp Gly Glu Trp Thr Tyr Asp Asp Ala Thr
            35                  40                  45
Lys Thr Phe Thr Val Thr Glu Lys Pro Glu Val Ile Asp Ala Ser Glu
        50                  55                  60
Leu Thr Pro Ala Val Thr
65                  70
```

<210> SEQ ID NO 21
<211> LENGTH: 55
<212> TYPE: PRT
<213> ORGANISM: Streptococcus dysgalactiae

<400> SEQUENCE: 21

```
Thr Tyr Lys Leu Val Ile Asn Gly Lys Thr Leu Lys Gly Glu Thr Thr
1               5                   10                  15
Thr Lys Ala Val Asp Ala Glu Thr Ala Glu Lys Ala Phe Lys Gln Tyr
                20                  25                  30
Ala Asn Asp Asn Gly Val Asp Gly Val Trp Thr Tyr Asp Asp Ala Thr
            35                  40                  45
Lys Thr Phe Thr Val Thr Glu
        50                  55
```

<210> SEQ ID NO 22
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 22

Gly Gly Gly Gly Gly Gly
1               5
```